US012575864B2

(12) United States Patent

Hsu et al.

(10) Patent No.: US 12,575,864 B2

(45) Date of Patent: **\*Mar. 17, 2026**

(54) INSERTER AND METHOD FOR SECURING AN IMPLANT TO A SPINAL PROCESS WITH A FLEXIBLE FASTENING SYSTEM

(71) Applicant: K2M, Inc., Leesburg, VA (US)

(72) Inventors: Brian Hsu, Greenwich (AU); Greg Mundis, Jr., Encinitas, CA (US); Burt Yaszay, San Diego, CA (US); Suken Shah, Wilmington, DE (US); Behrooz Akbarnia, La Jolla, CA (US); Catherine Stone, Arlington, VA (US); Brian Kunes, Washington, DC (US); Brandon Moore, Leesburg, VA (US)

(73) Assignee: K2M, Inc., Leesburg, VA (US)

(*) Notice: Subject to any disclaimer, the term of this patent is extended or adjusted under 35 U.S.C. 154(b) by 114 days.

This patent is subject to a terminal disclaimer.

(21) Appl. No.: 18/410,298

(22) Filed: Jan. 11, 2024

(65) Prior Publication Data

US 2024/0138884 A1 May 2, 2024

Related U.S. Application Data

(60) Continuation of application No. 16/857,711, filed on Apr. 24, 2020, now Pat. No. 11,896,269, which is a (Continued)

(51) Int. Cl.
*A61B 17/88* (2006.01)
*A61B 17/70* (2006.01)

(52) U.S. Cl.
CPC ...... *A61B 17/7083* (2013.01); *A61B 17/7032* (2013.01); *A61B 17/7053* (2013.01); *A61B 17/7076* (2013.01); *A61B 17/8869* (2013.01)

(58) Field of Classification Search
CPC ............ A61B 17/7083; A61B 17/7032; A61B 17/7053; A61B 17/7076; A61B 17/8869

(Continued)

(56) References Cited

U.S. PATENT DOCUMENTS

| | | | | |
|---|---|---|---|---|
| 1,346,940 A | * | 7/1920 | Collins | .............. A61B 17/8869 |
| | | | | 606/103 |
| 5,312,410 A | | 5/1994 | Miller et al. | |

(Continued)

FOREIGN PATENT DOCUMENTS

| | | |
|---|---|---|
| EP | 0649636 A2 | 4/1995 |
| EP | 2052689 A1 | 4/2009 |

(Continued)

OTHER PUBLICATIONS

Australian Search Report for Application No. AU 2016229822 dated Aug. 11, 2019, 1 page.

(Continued)

*Primary Examiner* — Eduardo C Robert
*Assistant Examiner* — David C Comstock
(74) *Attorney, Agent, or Firm* — Lerner David LLP

(57) ABSTRACT

A surgical instrument includes a body, a securement arm, a clamp lock, and a tensioning assembly. The body defines a longitudinal axis and has proximal and distal portions. The distal portion defines a recess. The securement arm is coupled to the body and translatable along the body in a direction parallel to the longitudinal axis between first and second position. The clamp lock is pivotally coupled to the distal portion of the body. The clamp lock is pivotable between secured and unsecured configurations. The tensioning assembly translatable in a direction parallel to the longitudinal axis between proximal and distal position. The tensioning assembly configured to draw a flexible band to tension the flexible band about a bony element.

18 Claims, 16 Drawing Sheets

Related U.S. Application Data continuation of application No. 15/980,956, filed on May 16, 2018, now Pat. No. 10,667,847, which is a division of application No. 15/258,123, filed on Sep. 7, 2016, now Pat. No. 9,999,450, which is a continuation of application No. 14/644,428, filed on Mar. 11, 2015, now Pat. No. 9,757,167.

(58) Field of Classification Search
     USPC ................... 606/86 A, 99, 74, 103, 324, 279
     See application file for complete search history.

(56)                    References Cited

U.S. PATENT DOCUMENTS

| | | | |
|---|---|---|---|
| 5,449,361 | A | 9/1995 | Preissman |
| 5,496,318 | A | 3/1996 | Howland et al. |
| 6,086,590 | A | 7/2000 | Margulies et al. |
| 8,029,513 | B2 | 10/2011 | Konno et al. |
| 8,162,946 | B2 | 4/2012 | Baccelli et al. |
| 8,465,495 | B2 | 6/2013 | Belliard |
| 8,486,110 | B2 | 7/2013 | Fielding et al. |
| 8,728,083 | B2 | 5/2014 | Baccelli et al. |
| 9,039,711 | B2 * | 5/2015 | Mickiewicz ....... A61B 17/8869 606/103 |
| 9,173,685 | B2 | 11/2015 | Lindquist et al. |
| 9,433,441 | B2 | 9/2016 | George et al. |
| 9,757,167 | B2 | 9/2017 | Hsu et al. |
| 9,999,450 | B2 * | 6/2018 | Hsu .................... A61B 17/7076 |
| 10,034,692 | B2 | 7/2018 | Palmer et al. |
| 10,548,644 | B2 | 2/2020 | George et al. |
| 10,575,879 | B2 | 3/2020 | Palmer et al. |
| 10,667,847 | B2 | 6/2020 | Hsu et al. |
| 11,896,269 | B2 * | 2/2024 | Hsu .................... A61B 17/7076 |
| 2002/0116013 | A1 | 8/2002 | Gleason et al. |
| 2005/0010220 | A1 * | 1/2005 | Casutt ................ A61B 17/7082 606/86 A |
| 2007/0270861 | A1 | 11/2007 | Leisinger |
| 2009/0054933 | A1 | 2/2009 | Mickiewicz et al. |
| 2009/0082821 | A1 | 3/2009 | Konno et al. |
| 2009/0138046 | A1 | 5/2009 | Altarac et al. |
| 2009/0138048 | A1 | 5/2009 | Baccelli et al. |
| 2009/0204118 | A1 | 8/2009 | Pratt |
| 2010/0185243 | A1 | 7/2010 | Pasquet et al. |
| 2011/0106185 | A1 | 5/2011 | Gil et al. |
| 2011/0238118 | A1 | 9/2011 | Baccelli et al. |
| 2011/0301644 | A1 | 12/2011 | Belliard |
| 2012/0271356 | A1 | 10/2012 | Ramsay et al. |
| 2013/0041410 | A1 | 2/2013 | Hestad et al. |
| 2013/0072983 | A1 | 3/2013 | Lindquist et al. |
| 2013/0261680 | A1 | 10/2013 | Baccelli et al. |
| 2014/0114356 | A1 | 4/2014 | Le Couedic et al. |
| 2014/0257397 | A1 | 9/2014 | Akbarnia et al. |
| 2014/0257400 | A1 | 9/2014 | George et al. |
| 2014/0277142 | A1 | 9/2014 | Blain et al. |
| 2016/0157896 | A1 | 6/2016 | Palmer et al. |
| 2016/0242819 | A1 | 8/2016 | Simpson et al. |
| 2016/0242825 | A1 * | 8/2016 | Simpson ............. A61B 17/842 |

FOREIGN PATENT DOCUMENTS

| | | | |
|---|---|---|---|
| EP | 2316363 | A1 | 5/2011 |
| WO | 2012176096 | A1 | 12/2012 |
| WO | 2013001180 | A1 | 1/2013 |

OTHER PUBLICATIONS

European Search Report dated Oct. 8, 2018 cited in EP Application No. 16762401.

European Search Report dated Jun. 18, 2014 issued in European Application No. 14158813.

International Search Report dated Jul. 26, 2016, issued in PCT/US16/21507.

International Preliminary Report on Patentability dated Sep. 12, 2017.

International Preliminary Report on Patentability dated Sep. 21, 2017.

* cited by examiner

FIG. 2     A

INSERTER AND METHOD FOR SECURING AN IMPLANT TO A SPINAL PROCESS WITH A FLEXIBLE FASTENING SYSTEM

CROSS-REFERENCE TO RELATED APPLICATIONS

This application is a continuation of U.S. patent application Ser. No. 16/857,711, filed Apr. 24, 2020, which is a continuation of U.S. patent application Ser. No. 15/980,956, filed May 16, 2018, which is a divisional of U.S. patent application Ser. No. 15/258,123, now U.S. Pat. No. 9,999, 450, filed Sep. 7, 2016, which is a continuation of U.S. patent application Ser. No. 14/644,428, now U.S. Pat. No. 9,757,167, filed Mar. 11, 2015. The entire contents of each of the above applications are hereby incorporated by reference.

BACKGROUND

1. Technical Field

The present disclosure relates to implants and, more specifically, to methods, flexible implant systems, and instruments for securing an implant to a bony element.

2. Discussion of Related Art

The spine is made up of a superposition of vertebrae, that are normally aligned along a vertebral axis, extending from the lumbar vertebrae to the cervical vertebrae, with each vertebra presenting a posterior wall from which a spinous process projects and two side edges having walls from which the ribs and/or transverse processes projects. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

The hooks are generally inserted in pairs in each vertebra and on either side close to the pedicles, the heads of the hooks projecting from the posterior wall of a vertebra, one on either side of the spinous process. The heads may be tulip-shaped to receive a rod that is secured by means of a set screw inserted in the head and bearing against the rod. Rows constituted by the heads of the hooks situated on either side of the spinous processes are interconnected and held in fixed position by two rods that are parallel to each other and to the axis of the spine.

The screws have tulip-shaped heads and are inserted in pairs in the posterior walls of vertebrae in the pedicles on either side of the spinous processes. The screws constitute fastening points in the vertebrae for holding them relative to one another. The screws are inserted into the pedicles of the vertebrae, and under certain circumstances, the pedicles may be damaged.

Therefore, a continuing need exists for an implant that can address the anatomy correction, including large deformity reductions and translations needed, and still maintain the safety of the patient. In addition, there is a need for instruments and methods for securing such an implant to a bony element of a patient.

SUMMARY

In an aspect of the present disclosure, a surgical instrument includes a body, a securement arm, a clamp lock, and a tensioning assembly. The body defines a longitudinal axis and has proximal and distal portions. The distal portion defines a recess. The securement arm is coupled to the body and is translatable along the body in a direction parallel to the longitudinal axis between first and second positions. The clamp lock is pivotally coupled to the distal portion of the body. The clamp lock is pivotable between secured and unsecured configurations. The tensioning assembly is translatable in a direction that is parallel to the longitudinal axis between proximal and distal positions. The tensioning assembly is configured to draw a flexible band to tension the flexible band about a bony element.

In aspects, the surgical instrument includes a securement screw that passes through a securement opening defined in the proximal portion of the body. The securement screw may be rotatably coupled to a distal end of the securement arm and may be configured to translate the securement arm between its first and second positions. The securement screw may include a threaded body and the walls that define the securement opening may include threads. The threaded body of the securement screw may engage the threads of the securement opening such that the securement arm translates in a direction that is parallel to the longitudinal axis in response to rotation of the securement screw. The securement arm may include securement fingers that define a passage therebetween. The distal portion of the body may be positioned within the passage.

In some aspects, the clamp lock includes a securement tab that is positioned on one end and defines a lock cam opening on the other end. The clamp lock may define a pivot pin opening positioned between the securement tab and the lock cam opening. The pivot pin opening may receive a pivot pin that is fixed to the distal portion of the body such that the clamp lock is pivotable about the pivot pin. The securement tab may be configured to engage a notch defined by a clamp received within the recess defined in the distal portion of the body to secure the clamp within the recess. The lock cam opening may receive a lock cam pin. The securement arm may include securement fingers where each securement finger defines a lock cam channel. The lock cam pin may be disposed within the lock cam channel of each of the securement fingers. In the proximal position of the securement arm, the walls defining the lock cam channels may engage the lock cam pin to secure the clamp lock in its secured configuration. In the distal position of the securement arm, the walls defining the lock cam channels may engage the lock cam pin to pivot the clamp lock to its unsecured position. The securement arm may have an intermediate position between its first and second position such that the clamp lock is pivotable between its secured and unsecured positions. The clamp lock may be biased towards the secured configuration.

In particular aspects, the surgical instrument includes a tensioning screw that passes through a tensioning opening defined in the proximal portion of the body. The tensioning screw may pass through a tensioning body of the tensioning assembly and may be configured to translate the tensioning assembly between the proximal and distal positions. The distal portion of the body may include a tensioning screw support arm that extends perpendicular to the longitudinal axis and defines a tensioning screw securement opening that rotatably receives a distal end of the tensioning screw.

In certain aspects, the tensioning assembly includes a button that defines a tensioning screw passage which receives a threaded body of the tensioning screw therein. The tensioning screw passage may be defined by a first wall that has a smooth surface and a second wall that includes threads. The button may have a disengaged position in which the second wall is engaged with the threaded body of the tensioning screw such that the tensioning assembly translates in a direction that is parallel to the longitudinal axis in response to rotation of the tensioning screw. The button may have a depressed position in which the second wall is disengaged from the threaded body of the tensioning screw such that the tensioning assembly is freely translatable over the threaded body parallel to the longitudinal axis irrespective of rotation of the tensioning screw. The tensioning assembly may include a button biasing member that is positioned to urge the button towards the disengaged position.

In aspects, the surgical instrument includes a band locking mechanism that is positioned on the tensioning assembly. The band locking mechanism may be configured to fix a flexible band to the tensioning assembly. The tensioning assembly may include first and second support arms. Each of the first and second support arms may define a pin opening that receives an end of the flexible band lock pivot pin. The band locking mechanism may include a locking lever that is pivotally supported about the flexible band lock pivot pin. The band locking mechanism may include an inner locking member and an outer locking member. The inner locking member may be pivotally coupled to a tensioning body of the tensioning assembly and may include an inner locking surface that faces the outer locking member. The outer locking member may include tabs that are connected by a connector. Each of the tabs may define a flexible band pin lock opening that slidably receives the band locking pin. The tabs may define opposing camming recesses that are configured to receive cam bosses defined on the locking lever. The locking lever may be pivotable between unlocked and locked configurations. As the locking lever is pivoted towards the locked configuration, the cam bosses may engage the tabs to move an outer locking surface, that is disposed on the outer locking member, towards the inner locking surface. The inner and outer locking surfaces may define a band passage therebetween and may be configured to fix a flexible band within the band passage when the locking lever is in its locked configuration.

In some aspects, the recess defined by the distal portion of the body is configured to receive a clamp. The securement arm may be configured to secure a rod within a clamp that is received in the recess defined by the distal portion of the body. In the secured configuration of the clamp lock, the clamp lock may be configured to secure a clamp within the recess defined by the distal portion of the body. The tensioning assembly may be configured to draw the flexible band through a clamp that is secured in the recess of the distal portion defining by the distal portion of the body.

In another aspect of the present disclosure, a method of surgery includes positioning a clamp within a recess defined in a distal portion of a body of a surgical instrument, positioning a rod within a rod cavity defined by the clamp, rotating a securement screw of the surgical instrument to translate a securement arm of the surgical instrument distally, passing ends of a flexible band that is positioned about a bony element through a slot of the clamp and through a band passage defined by a band locking mechanism of the surgical instrument, rotating a band locking lever of the band locking mechanism to a locked configuration to fix the flexible band within the band passage, rotating a tensioning screw to translate the locking mechanism proximally over the tensioning screw parallel to the longitudinal axis to tension the flexible band about the bony element, securing the clamp to the rod, securing the clamp to the flexible band, and releasing the clamp from the recess of the distal portion of the surgical interment. The body of the surgical instrument defines a longitudinal axis. The securement fingers of the securement arm may secure the rod within the rod cavity of the clamp when the securement arm is translated distally.

In aspects, positioning the clamp within the recess includes urging a clamp lock towards an unsecured configuration with the clamp as the clamp is positioned within the recess. The clamp lock may engage the clamp to secure the clamp within the recess when the clamp is positioned within the recess. Positioning the clamp within the recess may include rotating the securement screw to translate the securement arm to a fully proximal position. The securement arm may define lock cam channels that each have walls which engage a lock cam pin to pivot a clamp lock to an unsecured configuration. Rotating the securement screw may include pivoting the clamp lock to a secured configuration to secure the clamp within the clamp recess in response to distal translation of the securement arm. During subsequent distal translation of the securement arm, the wall defining the lock cam channel may engage the lock cam pin to fix the clamp lock in the secured configuration.

In some aspects, the method includes inserting a tool through an opening in the distal portion to engage a rod set screw to the clamp and rotating the tool such that the rod set screw is rotated to partially secure the rod within the rod cavity of the clamp after rotating the securement screw of the surgical instrument to translate the securement arm of the surgical instrument and before passing ends of the flexible band through the slot of the clamp. Securing the clamp to the rod may include inserting a tool through an opening in the distal portion to engage a rod set screw of the clamp and rotating the tool such that the rod set screw is rotated to secure the rod within the rod cavity of the clamp.

In particular aspects, the method includes depressing a button of a tensioning assembly and translating the tensioning assembly proximally over the tensioning screw to a distal position before rotating the band locking lever of the band locking member to the locked configuration. The method may include rotating the tensioning screw to translate the locking mechanism to a distal position before pivoting the band locking lever of the band locking member to the locked configuration.

In certain aspects, rotating the band locking lever includes engaging an outer locking member with camming bosses of the band locking lever to move the outer locking member towards an inner locking member. The band passage may be defined between locking surfaces of the inner and outer locking members. Securing the clamp to the flexible band may include inserting a tool through an opening in the distal portion to engage a band set screw of the clamp and rotating the tool such that the band set screw is rotated to secure the flexible band within the rod cavity of the clamp. Releasing the clamp may include rotating the securement screw to translate the securement arm to a fully proximal position. The securement arm may define lock cam channels that have walls which engage a lock cam pin to pivot a clamp lock to an unsecured configuration. The method may include trimming the flexible band to length adjacent the clamp after securing the flexible band to the clamp.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
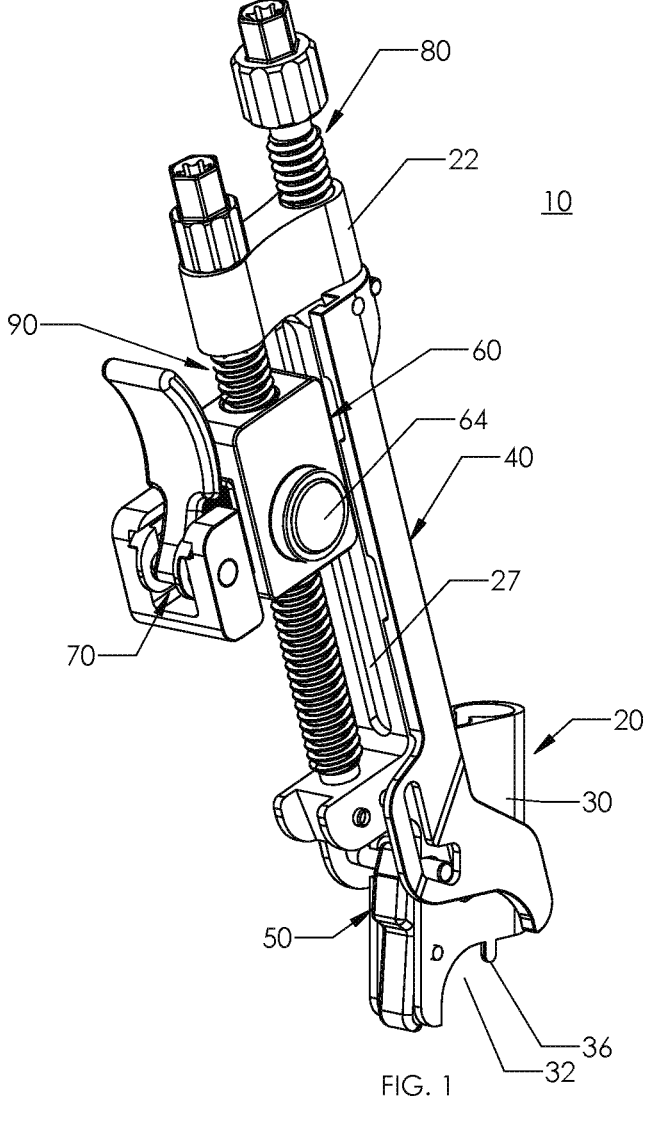
FIG. 1 is a perspective view of an inserter provided in accordance with the present disclosure.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. Additionally, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

This disclosure relates generally to an instrument and method for securing a flexible implant system to a bony element of a patient. The flexible implant system includes a clamp and a flexible band that wraps around a bony element. The instrument secures to the clamp such that a clinician may draw the flexible band through the clamp and secure the clamp to a rod. Then, the clinician uses the instrument to tension the flexible band about the bony element and to fix the flexible band to the clamp. For a detailed description of a suitable implant or clamp, reference may be made to commonly owned U.S. Patent Application Publication No. 2014/0257397, the entire contents of this application are hereby incorporated by reference.

Figure 2:
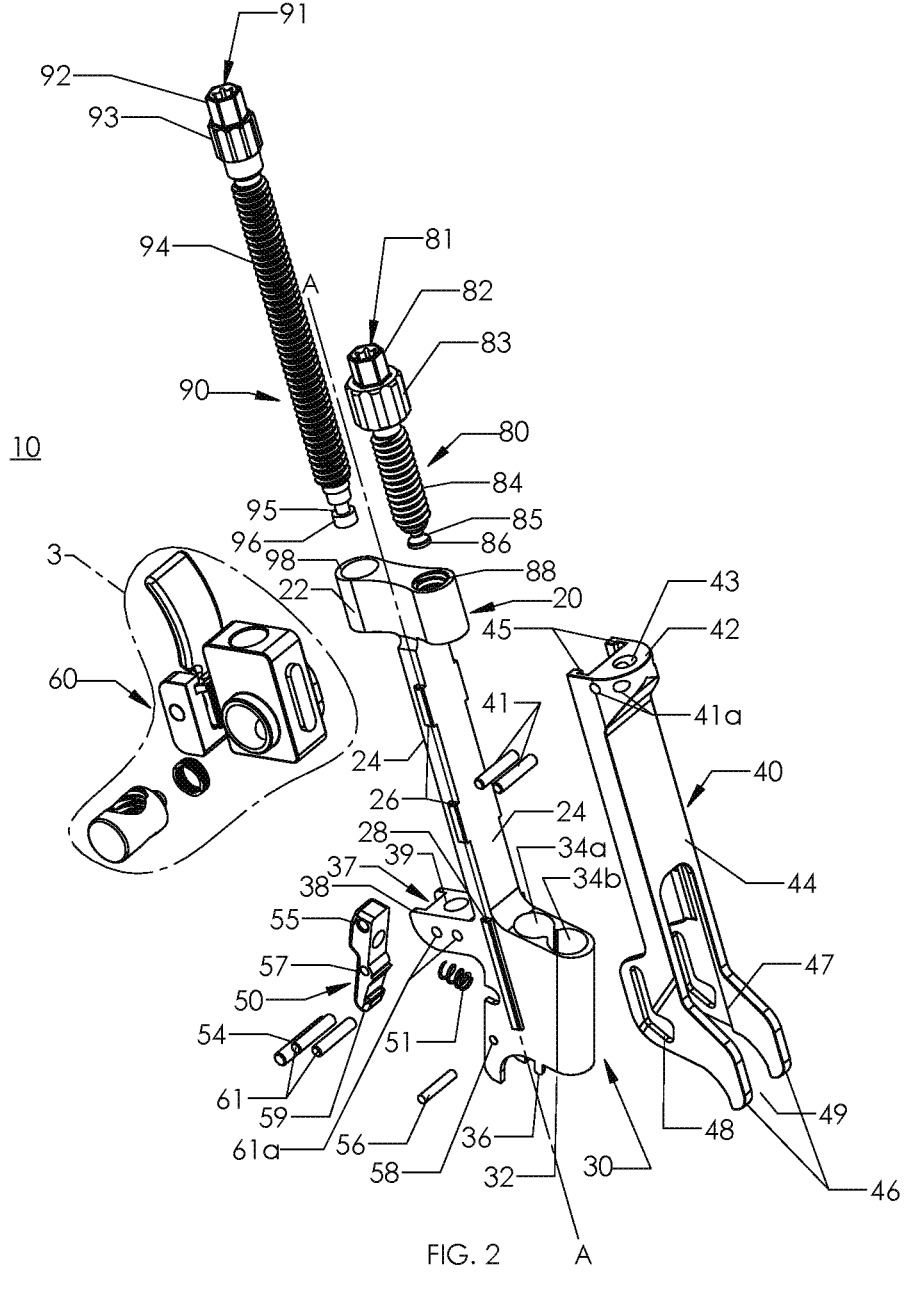
FIG. 2 is an exploded perspective view, with parts separated, of the inserter of FIG. 1.

Referring now to FIGS. 1 and 2, a surgical instrument or inserter 10 is provided in accordance with the present disclosure and includes a body 20, a securement arm 40, a clamp lock 50, a tensioning assembly 60, a securement screw 80, and a tensioning screw 90. The body 20 includes a proximal portion 22, a central portion 24 extending from the proximal portion 22, and a distal portion 30 extending from the central portion 24. The central portion 24 defines a longitudinal axis A-A. The proximal portion 22 is substantially rectangular in cross-section and is orthogonal to the longitudinal axis A-A with first and second ends extending beyond the central portion 24. The first end defines a securement screw opening 88 that extends parallel to the longitudinal axis A-A and that is threaded to cooperate with threads of the securement screw 80 as detailed below. The second end defines a tensioner screw opening 98 that extends parallel to the longitudinal axis A-A and that is dimensioned to allow the tensioning screw 90 to freely rotate relative to the proximal portion 22. The central portion 24 includes central arm guides 26 and the distal portion 30 includes distal arm guides 28 positioned on opposite sides of the body 20 parallel to the longitudinal axis A-A.

Figure 5:
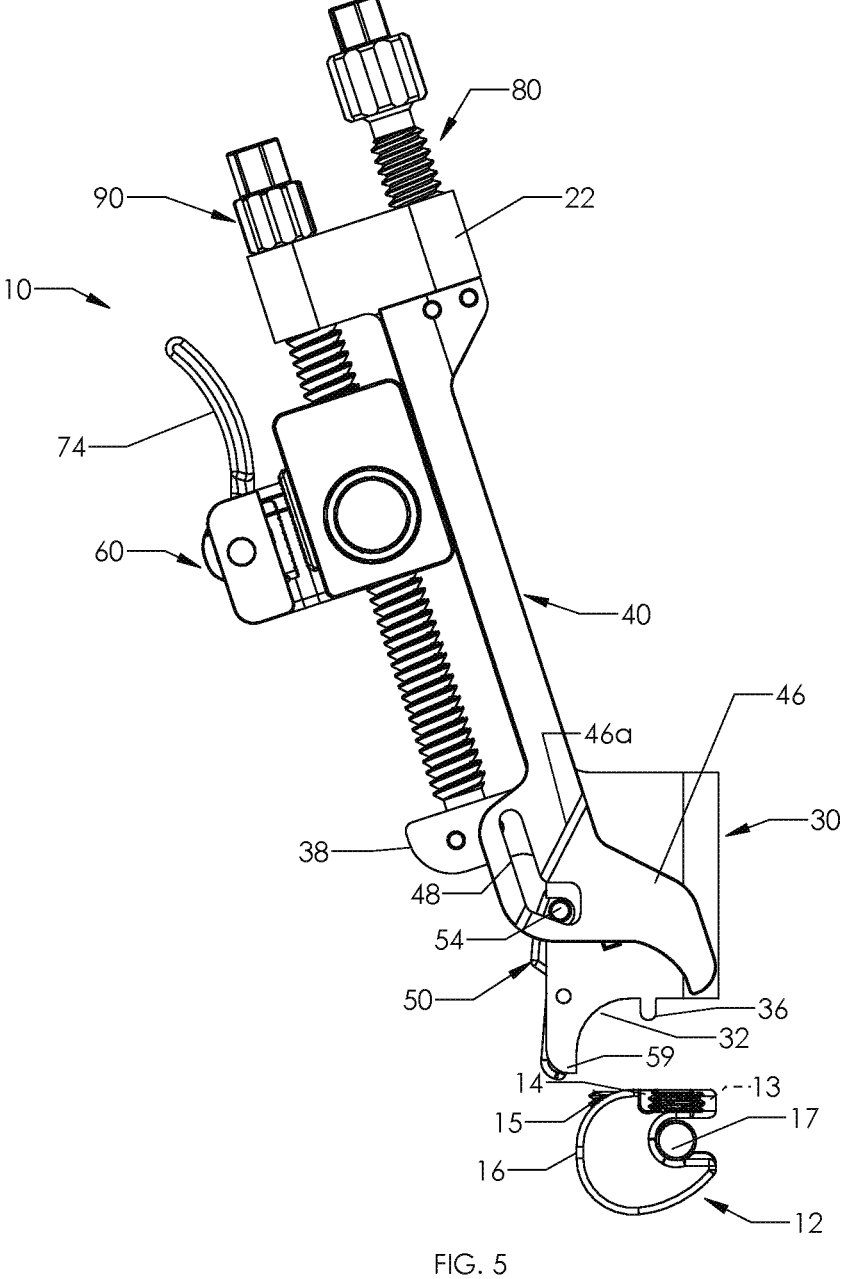
FIG. 5 is a side view of the inserter of FIG. 1 in with a securement arm of the inserter in an intermediate position and an clamp positioned below a clamp recess of the inserter.

The distal portion 30 receives and secures an implant or clamp 12 (FIG. 5) to the inserter 10. The distal portion 30 defines a clamp receiver 32 that is dimensioned and shaped to receive the clamp 12. The distal portion 30 includes an alignment tab 36 for engaging a corresponding alignment notch 14 defined by the clamp 12 to align the clamp 12 with the clamp receiver 32. The distal portion 30 also defines tool openings 34a, 34b that extend through the distal portion 30 and into the clamp receiver 32 (FIG. 5). The tool openings 34a, 34b extend parallel to one another and are offset from the longitudinal axis A-A by an angle θ (FIG. 10) to provide clearance for a tool as detailed below. The angle θ may be in a range of about 15° to about 45° (e.g., about 30°). The tool openings 34a, 34b are sized to receive tools for manipulating the clamp 12 secured in the clamp receiver 32 as detailed below.

The securement arm 40 is slidable relative to the body 20 to lock the clamp 12 within the clamp receiver 32 and retain a rod 19 (FIG. 8) within the clamp 12 as detailed below. The securement arm 40 includes a proximal end portion 42, an arm body 44, and distal securement fingers 46. The proximal end portion 42 defines a securement screw opening 43 that receives a distal retainer 86 of the securement screw 80 as detailed below. The arm body 44 extends from the proximal end portion 42 parallel to the longitudinal axis A-A. The proximal end portion 42 and the arm body 44 define a guide channel 45 that slidably receives central and distal arm guides 26, 28 of the body 20. The securement fingers 46 extend from the arm body 44 and define a passage 49 therebetween. The securement fingers 46 are positioned on either side of the distal portion 30 of the body 20 such that the distal portion 30 is positioned within the passage 49. Each of the securement fingers 46 also defines a guide shelf 47 that slides along surfaces of the distal guides 28 of the distal portion 30. Each retention arm 46 also defines a lock cam channel 48 that receives a lock cam pin 54. As discussed in greater detail below, the lock cam channel 48 engages the lock cam pin 54 as the securement arm 40 is translated to pivot the clamp lock 50 such that the clamp 12 is within the clamp receiver 32 of the distal portion 30.

Figure 8:
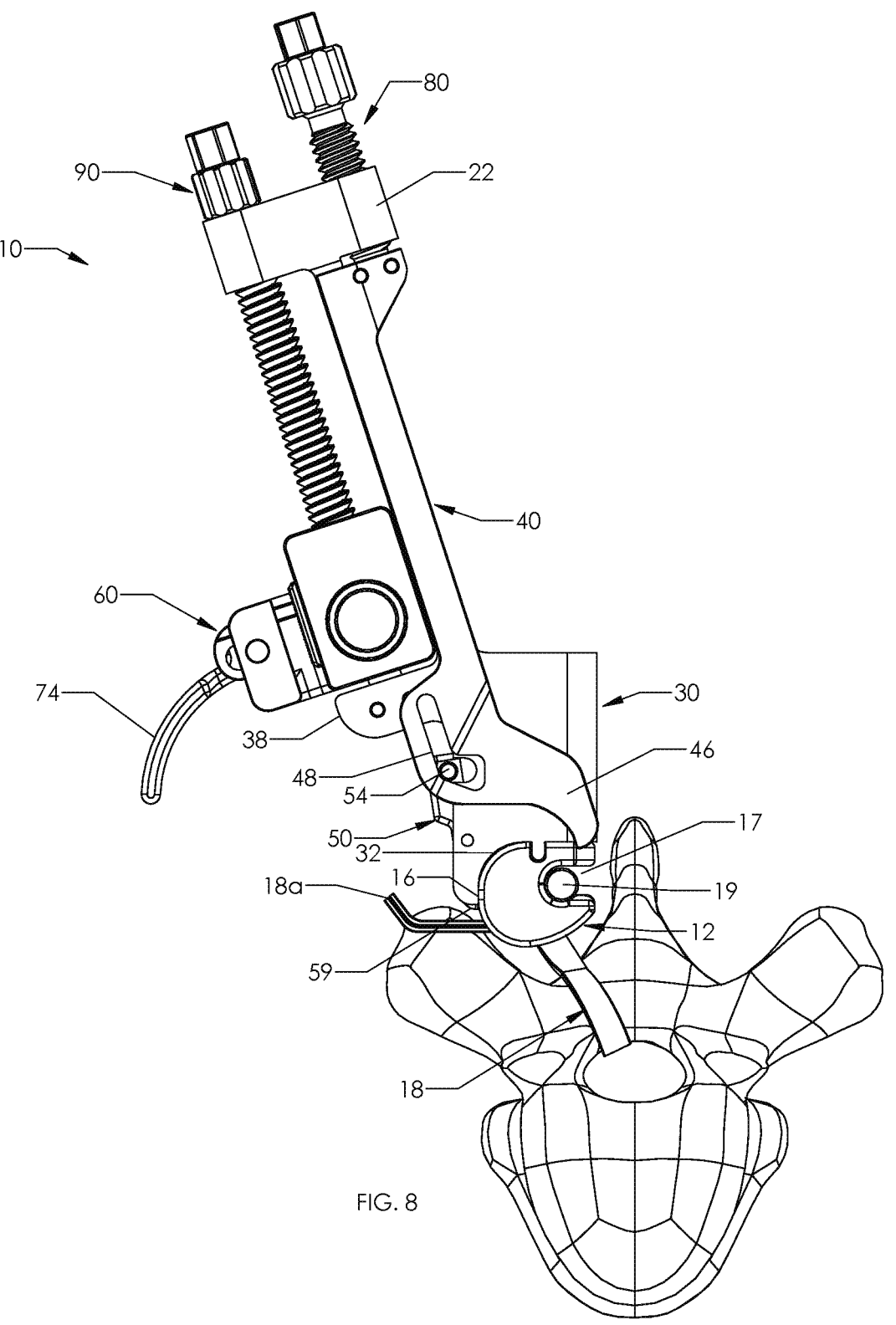
FIG. 8 is a side view of the inserter of FIG. 7 with a rod received in the clamp.
Figure 9:
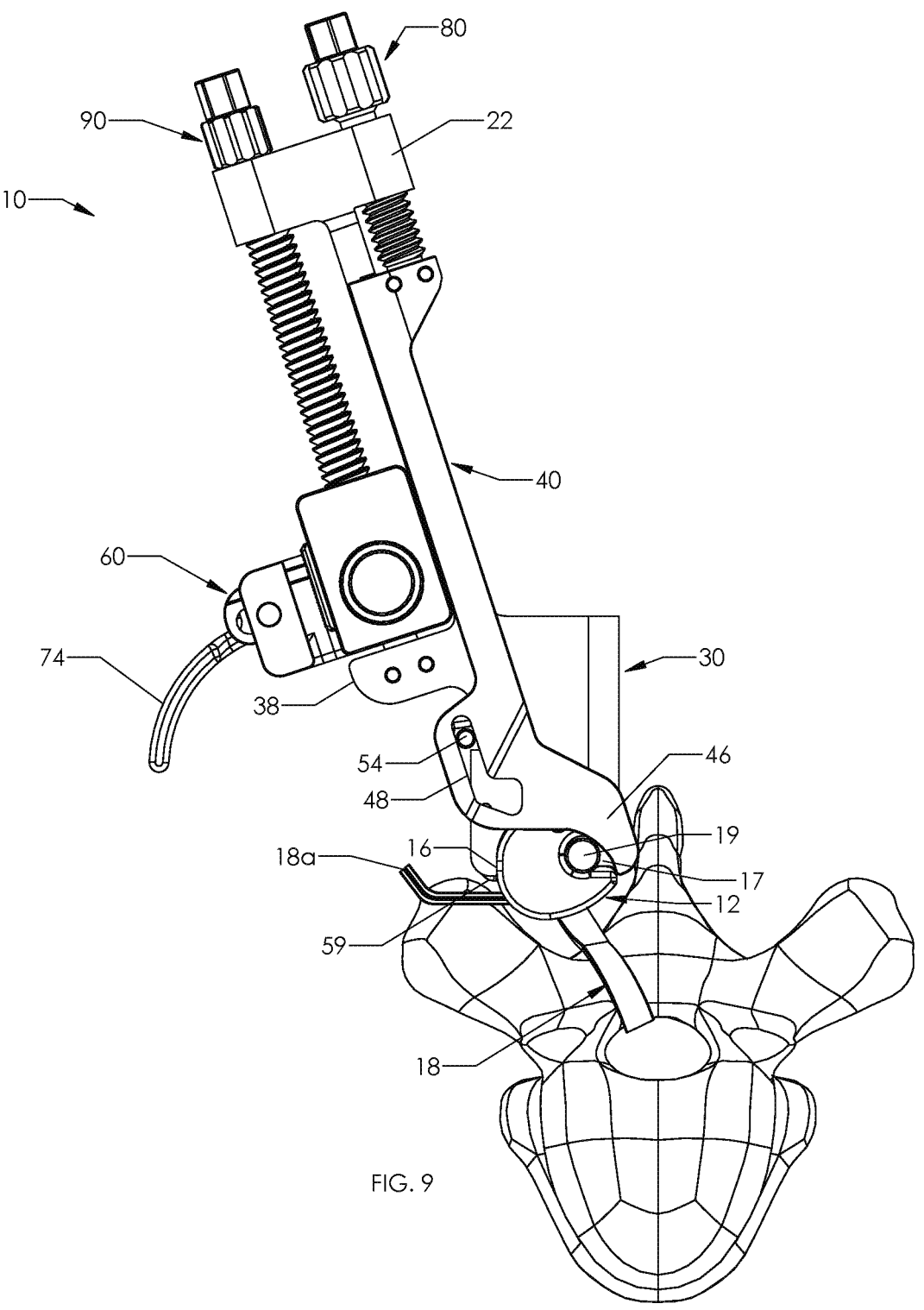
FIG. 9 is a side view of the inserter of FIG. 8 in with the securement arm in a distal position.

The securement screw 80 is rotatable to translate the securement arm 40 parallel to the longitudinal axis A-A of the inserter 10 between a first or proximal position (FIG. 6), an intermediate position (FIG. 8), and a second or distal position (FIG. 9). The securement screw 80 includes a head 81, a threaded body 84, and a distal retainer 86. The head 81 includes a tool engagement portion 82 proximal to a finger engagement portion 83. The tool engagement portion 82 is dimensioned and shaped to be engaged by a tool (not explicitly shown) to rotate the securement screw 80. For example, the tool engagement portion 82 may define a recess that is engagable with a torx or star-shaped screwdriver. Additionally or alternatively, the tool engagement portion 82 may have a hexagonal outer surface that is engagable with a wrench or a socket. The finger engagement portion 83 is sized and shaped to be engaged by fingers of a clinician to rotate the securement screw 80. For example, the finger engagement portion 83 may include a knurled outer surface. Additionally or alternatively, the outer surface of the finger engagement portion 83 may include a plurality of raised surfaces with grooves between the raised surfaces to provide a gripping surface for fingers of a clinician.

The threaded body 84 of the securement screw 80 extends distally from the head 81 parallel to the longitudinal axis A-A. The distal retainer 86 is spaced apart from the threaded body 84 to define a retention recess 85 between the threaded body 84 and the distal retainer 86. The threaded body 84 passes through and cooperates with threads on the inner surface of the securement screw opening 88 defined in the proximal portion 22 of the body 20. A portion of the head 81 (e.g., finger engagement portion 83) is larger than the threaded body 84 to prevent the securement screw 80 from passing entirely through the securement screw opening 88. The distal retainer 86 passes through the securement screw opening 43 defined in the proximal end portion 42 of the securement arm 40. The proximal end portion 42 defines openings 41a that receive retention pins 41. Each of the retention pins 41 pass through the retention recess 85 of the securement screw 80 such that the securement screw 80 passing between the retention pins 41 to rotatably receive and longitudinally fix the distal retainer 86 of the securement screw within the proximal end portion 42 of the securement arm 40. Thus, allowing the securement screw 80 to rotate relative to the securement arm 40 such that as the securement screw 80 is rotated, the securement screw 80 translates the securement arm 40 between its proximal and distal positions as detailed below.

With continued reference to FIG. 2, the clamp lock 50 engages the clamp 12 to secure the clamp 12 (FIG. 6) in the clamp receiver 32 of the distal portion 30. A proximal end of the clamp lock 50 defines a lock cam opening 55 and a distal end of the clamp lock 50 includes a locking tab 59 facing the clamp receiver 32. The clamp lock 50 defines a pivot pin opening 57 between the lock cam opening 55 and the locking tab 59. The distal portion 30 defines a pivot pin passage 58 that receives a pivot pin 56 which passes through the pivot pin opening 57 of the clamp lock 50 to pivotally secure the clamp lock 50 to the distal portion 30 of the body 20.

Figure 6:
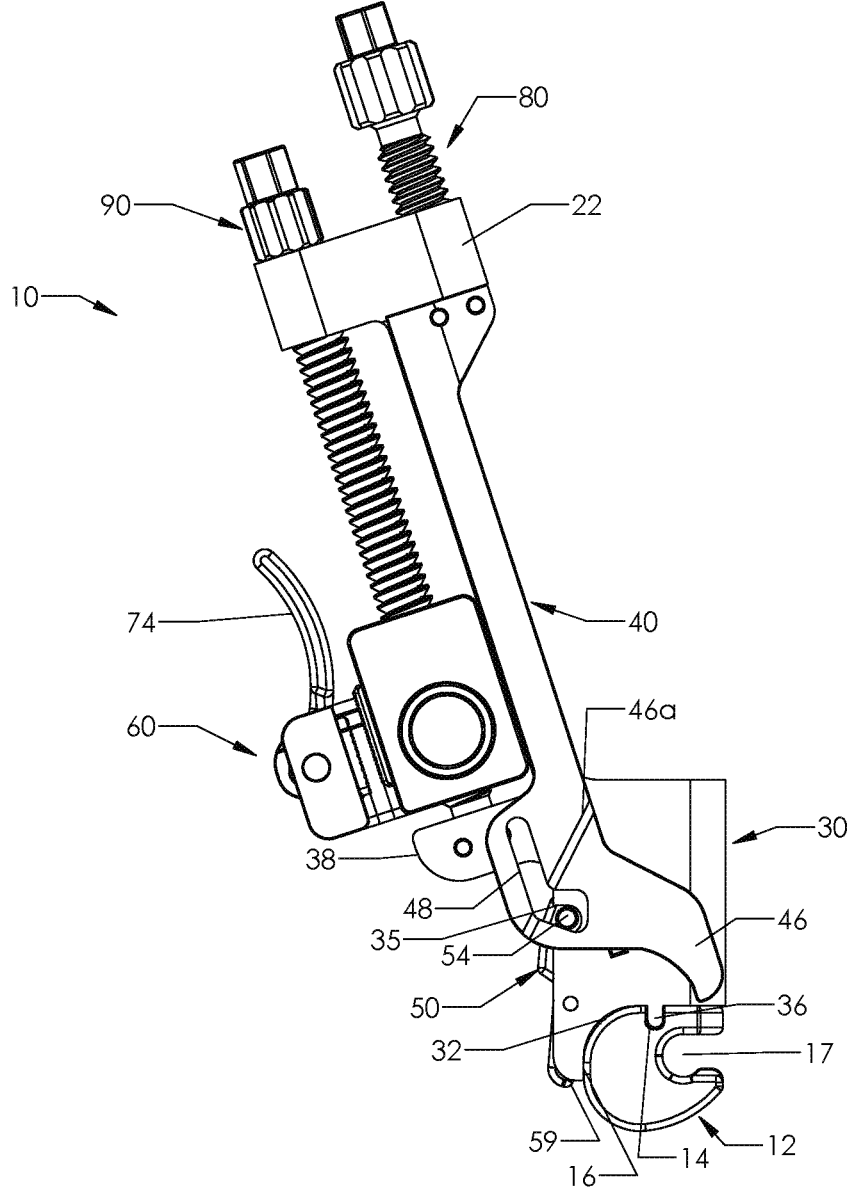
FIG. 6 is a side view of the inserter of FIG. 1 with the clamp positioned within the clamp of the inserter and the securement arm of the inserter in a proximal position such that a clamp lock is in an unsecured configuration.

The clamp lock 50 is pivotable between a secured configuration (FIG. 5) and an unsecured configuration (FIG. 6). In the secured configuration, the locking tab 59 of the clamp lock 50 is positioned to engage a notch 16 of the clamp 12 to secure the clamp 12 within the clamp receiver 32. In the unsecured configuration, the locking tab 59 is positioned away from the clamp 12 such that the clamp 12 is moveable into or out of the clamp receiver 32. The clamp lock 50 may include a lock biasing member 51 positioned between the distal portion 30 and the clamp lock 50 that engages the clamp lock 50 between the pivot pin opening 57 and the lock cam opening 55 to urge the clamp lock 50 towards the secured position. The clamp lock 50 may define a recess for receiving an end of the lock biasing member 51. The distal portion 30 may also define a cam notch 35 that receives the cam pin 54 when the clamp lock 50 is in the unsecured position.

With additional reference to FIG. 3, the tensioning assembly 60 is secured to a flexible band 18 (FIG. 11) to tension the flexible band 18 about a bony element as the tensioning screw 90 is rotated as detailed below. The tensioning assembly 60 includes a tensioning body 62, a button 64, and a band locking mechanism 70. The tensioning body 62 defines a tensioning screw channel 142 that passes through the tensioning body 62 parallel to the longitudinal axis A-A when the inserter 10 is assembled. A surface 62c of the tensioning body 62 facing the central portion 22 of the body 20 of the inserter 10 includes a guide nub 148 that is slidably received within a tensioner guide channel 27 (FIG. 1) defined in a surface of the central portion 22 of the body 20 facing the tensioning assembly 60. The tensioning body 62 also defines a button well 146 in one side surface 65a that passes through the majority of the tensioning body 62 orthogonal to and through the tensioning screw channel 142 that is sized to receive the button 64. A button ring 144 may extend from this side surface 62a of the tensioning body 62 around the outer perimeter of the button well 146. As shown in FIG. 4, the opposite side surface 62b of the tensioning body 62 may define an extension opening 155 that is axially aligned with the button well 146.

Figure 3:
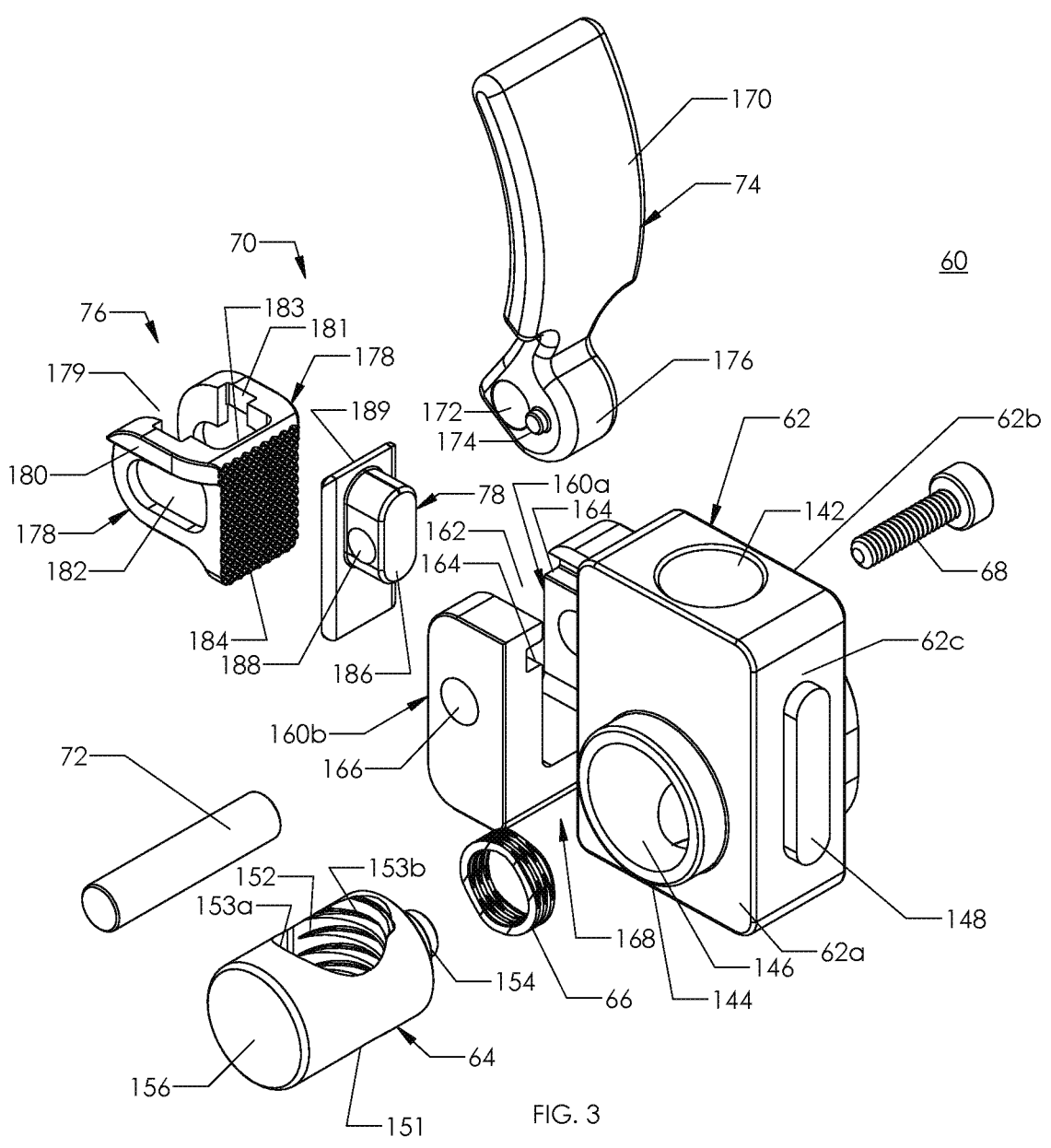
FIG. 3 is an enlarged view, with parts separated, of the indicated area of detail of FIG. 2.
Figure 4:
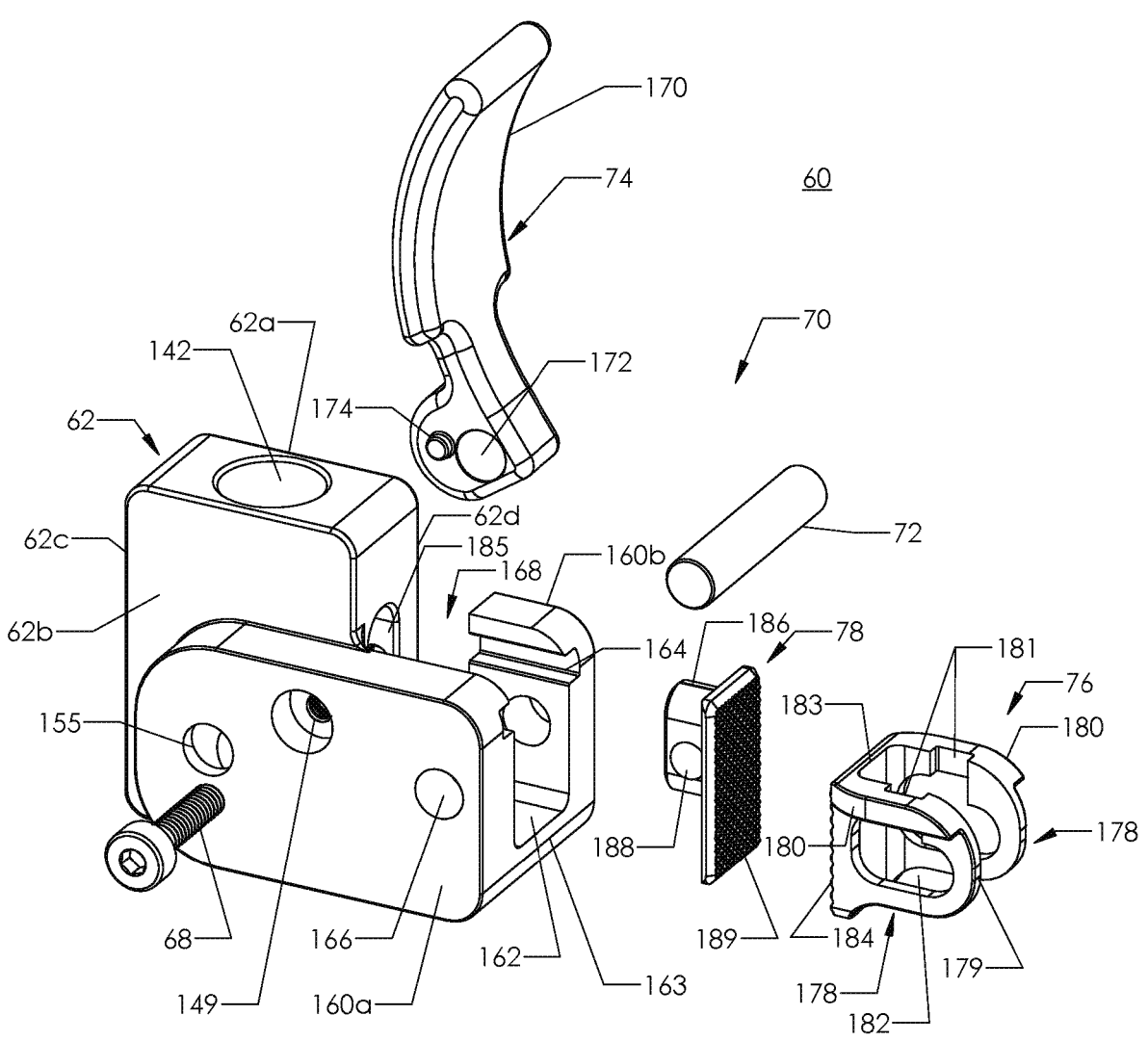
FIG. 4 is a rear perspective view, with parts separated, of the tensioning assembly of FIG. 3.

With continued reference to FIG. 3, the button 64 has a substantially cylindrical body 151 and includes a button extension 154 that extends from one end of the cylindrical body 151. The button extension 154 has a diameter that is less than the diameter of the cylindrical body 151. The other end of the cylindrical body 151 includes defines an engagement surface 156. The cylindrical body 151 defines a tensioning screw passage 152 that passes through the cylindrical body 151 at a location between the button extension 154 and the engagement surface 156. The tensioning screw passage 152 defines an oblong shape and is larger than the tensioning screw 90 (FIG. 2). The tensioning screw passage 152 is defined by a first wall or clearance 153*a* that has a substantially smooth surface and a second wall 153*b* that is threaded to engage threads of the tensioning screw 90 as detailed below. The first wall 153*a* is positioned adjacent the engagement surface 156 of the button 64 and the second wall 153*b* is positioned adjacent the button extension 154. As shown, each of the first and second walls 153*a*, 153*b* define half of the tensioning screw passage 152; however, it is contemplated that one of the first or second walls 153*a*, 153*b* may define more than half (e.g., 75%) of the tensioner screw passage 152 with the other one of the first or second walls 153*a*, 153*b* defining the remainder (e.g., 25%) of the tensioning screw passage 152.

The button 64 is positioned within the button well 146 of the tensioning body 62 with a button biasing member 66 positioned about the button extension 154 between the cylindrical body 151 and the side surface 62*b* of the body 62 such that the button 64 is biased out of the button well 146. As shown, the button biasing member 66 is in the form of a series of stacked Belleville washers; however, other biasing members are also contemplated including, but not limited to, coil springs. As discussed in detail below, the tensioning screw 90 passes through the tensioning screw channel 142 of the tensioning body 62 and the tensioning screw passage 152 of the button 64 to retain the button 64 within the button well 146.

Figure 12:
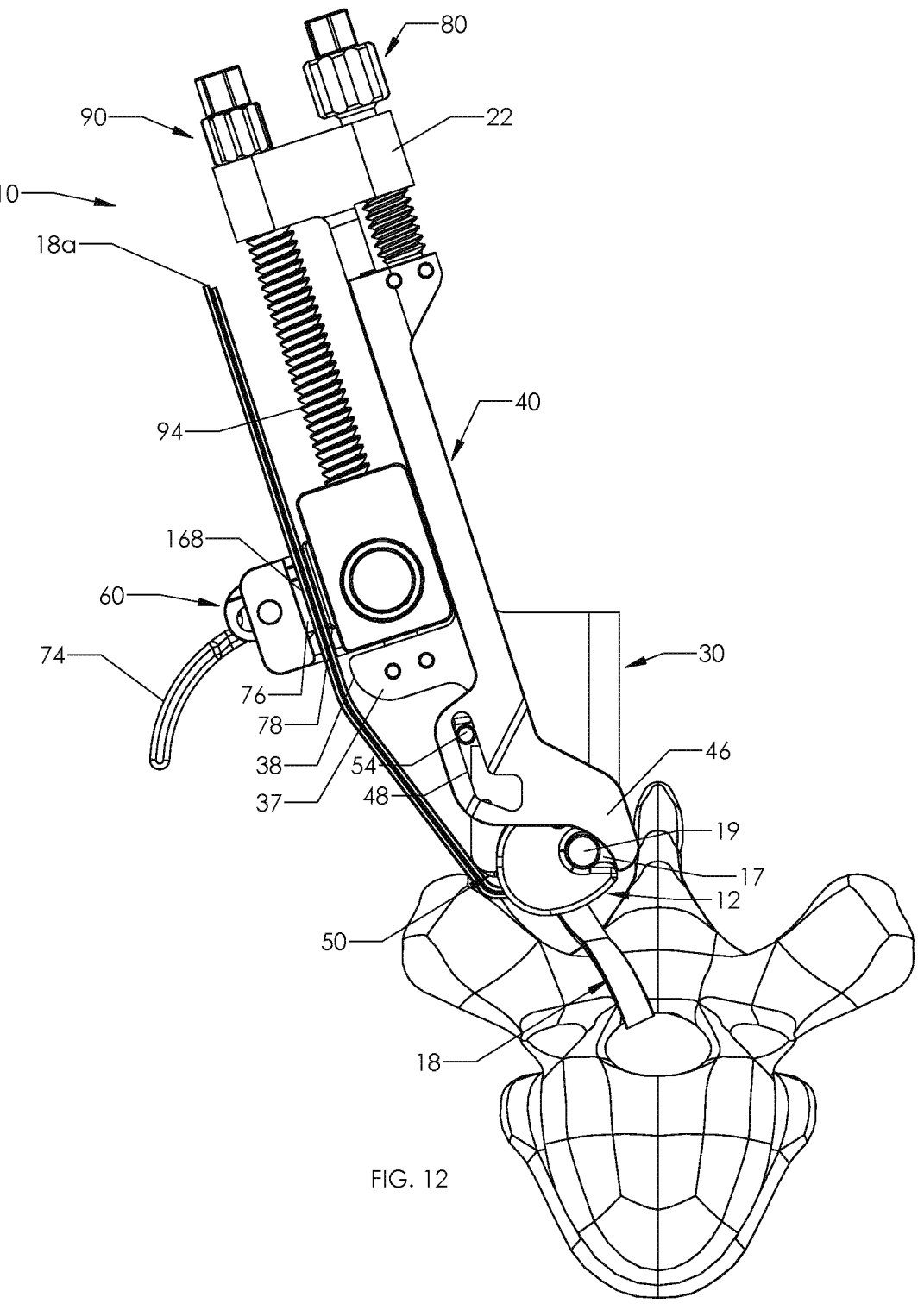
FIG. 12 is a side view of the inserter of FIG. 11 with the tensioning assembly in a distal position.

The button 64 has a disengaged position (FIG. 1) and a depressed position (FIG. 12). In the disengaged position, the button biasing member 66 urges the threads of the second wall 153*b* into engagement with a threaded body 94 of the tensioning screw 90. In the depressed position, the button 64 is depressed against the button biasing member 66 such that the threads of the second wall 153*b* are disengaged from the threaded body 94 of the tensioning screw 90. In the depressed position, the button extension 154 may be positioned within the extension opening 155 to provide enough clearance for the second wall 153*b* to disengage the threaded body 94. Further, in the depressed position, the first wall 153*a* may abut the threaded body 94 of the tensioning screw 90.

The tensioning screw 90 includes a head 91, the threaded body 94, and a distal retainer 96. The head 91 includes a tool engagement portion 92 proximal to a finger engagement portion 93. The tool engagement portion 92 is dimensioned and shaped to be engaged by a tool (not explicitly shown) to rotate the tensioning screw 90. For example, the tool engagement portion 92 may define a recess that is engagable with a torx or star-shaped screwdriver. Additionally or alternatively, the tool engagement portion 92 may have a hexagonal outer surface that is engagable with a wrench or a socket. The finger engagement portion 93 is sized and shaped to be engaged by fingers of a clinician to rotate the tensioning screw 90. For example, the finger engagement portion 93 may include a knurled outer surface. Additionally or alternatively, the outer surface of the finger engagement portion 93 may include a plurality of raised surfaces with grooves between the raised surfaces to provide a gripping surface for fingers of a clinician.

The threaded body 94 of the tensioning screw 90 extends distally from the head 91 parallel to the longitudinal axis A-A (FIG. 2). The distal retainer 96 is spaced apart from the threaded body 94 to define a retention recess 95 between the threaded body 94 and the distal retainer 96. The threaded body 94 passes through the tensioning screw opening 98 defined in the proximal portion 22 of the body 20. The tensioning screw opening 98 is sized to permit the threaded body 94 of the tensioning screw 90 to rotate freely. A portion of the head 91 (e.g., finger engagement portion 93) is larger than the threaded body 94 to prevent the tensioning screw 90 from passing entirely through the tensioning screw opening 98.

Referring briefly back to FIG. 2, the distal portion 30 includes a tensioning screw securement arm 37 that extends orthogonal to the longitudinal axis A-A (FIG. 2). The tensioning screw securement arm 37 also defines a tensioning screw securement opening 39 that is aligned with the tensioning screw opening 98 defined in the proximal portion 20. The distal retainer 96 of the tensioning screw 90 passes through the tensioning screw securement opening 39 defined in the tensioning screw securement arm 37 of the distal portion 30. Each of the retention pins 61 pass through the retention recess 95 of the tensioning screw 90 such that the tensioning screw 90 passes between the retention pins 61 to rotatably receive and longitudinally fix the distal retainer 96 of the tensioning screw 90 within the tensioning screw securement arm 37 of the distal portion 30. Thus, allowing the tensioning screw 90 to rotate relative to the tensioning screw securement arm 37. As detailed below as the tensioning screw 90 is rotated, the tensioning screw 90 translates the tensioning assembly 60 parallel to the longitudinal axis A-A (FIG. 2) between a proximal position (FIG. 14) and a distal position (FIG. 12).

With reference to FIGS. 3 and 4, the band locking mechanism 70 secures a flexible band 18 (FIG. 7) to the tensioning assembly 60 such that the tensioning assembly 60 may draw the flexible band 18 through the clamp 12 to tension the flexible band 18 about a bony element as detailed below. The band locking mechanism 70 includes band locking lever 74, an outer locking member 76, and an inner locking member 78. First and second support arms 160*a*, 160*b* support the band locking lever 74 and the outer locking member 76 to the tensioning body 62. The first support arm 160*a* is fixed to the side surface 62*b* of the tensioning body 62 opposite the side surface 62*a* that defines the button well 146. The first support arm 160*a* extends past a surface 62*d* of the tensioning body 62 and away from the surface 62*c* of the tensioning body 62, which includes the guide nub 148, such that the first support arm 160*a* extends away from the body 20 of the inserter 10. The first support arm 160*a* extends orthogonal to the body 20 of the inserter 10. The second support arm 160*b* is spaced apart from the first support arm 160*a* and is supported by a bridge 163 that extends from the first support arm 160*a*. The second support arm 160*b* and the bridge 163 define a band passage 168 with a surface of the tensioning body 62 opposite the guide nub 148. The first support arm 160*a* may act as a back stop to the band passage 168 as detailed below.

The first and second support arms 160*a*, 160*b* define a lock channel 162 therebetween. The first and second support arms 160*a*, 160*b* each define a lock guide channel 164 in a surface opposing the other support arm 160*a*, 160*b* that is orthogonal to the band passage 168 and in communication with the lock channel 162. Each of the first and second support arms 160*a*, 160*b* also defines a pin opening 166 that passes through the lock channel 162. The pin openings 166 oppose ends that receive an end of a band lock pivot pin 72. As detailed below, the band lock pivot pin 72 supports the band locking lever 74 and the outer locking member 76.

The band locking lever 74 defines a pin opening 172 and includes a lever arm 170, cam bosses 174, and a camming surface 176. The pin opening 172 is sized to rotatably receive the band lock pivot pin 72 therethrough to support the band locking lever 74. The lever arm 170 extends from the pin opening 172. The cam bosses 174 are positioned adjacent the pin opening 172 and extend parallel to an axis defined by the pin opening 172. The camming surface 176 is disposed on an outer surface of the band locking lever 74 about the pin opening 172.

The outer locking member 76 includes tabs 178 that are joined by a connector 183 and define a lever channel 179 therebetween. The tabs 178 extend parallel to one another and in the same direction from the connector 183. Each of the tabs 178 defines a pin slot 182 that slidably receives the band locking pin 72 such that each tab 178 is positioned between the band locking lever 74 and a respective one of the first and second support arms 160a, 160b. Each of the tabs 178 includes a slide 180 that is positioned along one side of the pin slot 182 and extends towards the respective one of the first and second support arms 160a, 160b. Each slide 180 is slidably received in the lock guide channel 164 defined in the respective one of the first and second support arms 160a, 160b. The slides 180 of the outer locking member 76 are slidable within the lock guide channels 164 such that the outer locking member 76 is slidable towards and away from the surface 62d of the tensioning body 62.

The band locking lever 74 is rotatable about the band locking pin 72 to move the outer locking member 76 towards and away from the surface 62d of the tensioning body 62. Each of the tabs 178 defines the band locking slot 182 that slidably receive the band locking pin 72. Tabs 178 also define camming recesses 181 that oppose one another. The camming recesses 181 are in communication with the lever channel 179 and are defined in an inner surface of each of the tabs 178 opposite the slides 180. Each of the camming recesses 181 receives one of the cam bosses 174 of the band locking lever 74 to move the outer locking member 76 towards and away from the tensioning body 62 in response to rotation of the band locking lever 74 as detailed below. Walls defining the camming recesses 181 may also limit the rotation of the band locking lever 74 about the band locking pin 72. The connector 183 includes a textured locking surface 184 that faces the tensioning body 62 and that is positioned within the band passage 168. The textured locking surface 184 may include a plurality of protrusions that engage a flexible band 18 (FIG. 11) disposed within the band passage 168 as discussed in greater detail below.

With continued reference to FIGS. 3 and 4, the inner locking member 78 includes a textured locking surface 189 that is positioned within the band passage 168 and in opposition to the textured locking surface 184 of the outer locking member 78. The textured locking surface 189 is substantially similar to the textured locking surface 184 of the outer locking member 76. The inner locking member 78 is pivotally coupled to the tensioning body 62 by a protrusion 186 that extends from the textured locking surface 189 towards the tensioning body 62.

The protrusion 186 defines a retention opening 188 that receives a retention screw 68 therethrough to fix the inner locking member 78 to the tensioning body 62. The tensioning body 62 defines an opening 185 in the surface 62d that receives the protrusion 186 of the inner locking member 78. With particular reference to FIG. 4, the tensioning body 62 defines a retention screw opening 149 that passes through the opening 185. A portion of the retention screw opening 149 is threaded. The retention screw 68 is threaded through the retention screw opening 149 and passes through the retention opening 188 of the inner locking member 78 to secure the inner locking member 78 within the opening 185 of the tensioning body 62. The retention screw opening 149 may also pass through the first support arm 160a.

Figure 13:
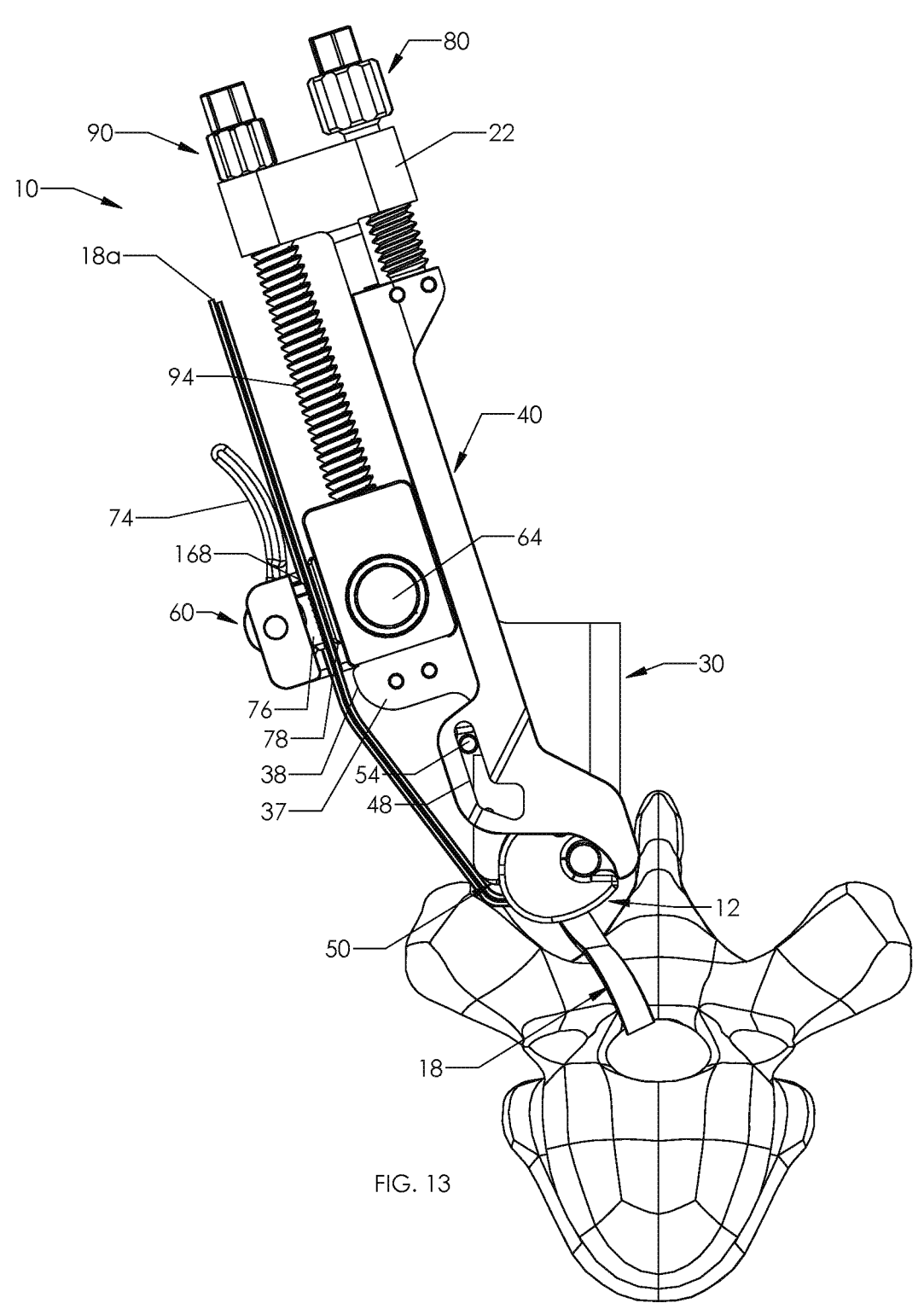
FIG. 13 is a side view of the inserter of FIG. 12 with the band locking mechanism in a locked configuration.

The locking mechanism 70 is moveable between an unlocked configuration (FIG. 12) and a locked configuration (FIG. 13). In the locked configuration, the lever arm 170 of the locking lever 74 is substantially parallel to the longitudinal axis A-A (FIG. 2) such that the locking mechanism 70 engages a flexible band 18 disposed within the band passage 168 between the locking surfaces 184, 189 of the inner and outer locking members 76, 78, respectively, to fix the flexible band 18 relative to the tensioning body 62. In the unlocked configuration, the lever arm 170 of the locking lever 74 is substantially perpendicular to the longitudinal axis of the inerter 10 such that a flexible band 18 is slidable through the band passage 168 between the locking surfaces 184, 189 of the inner and outer locking members 76, 78, respectively. As the band locking lever 74 is rotated about the band locking pin 72 towards the unlocked configuration, the cam bosses 174 of the band locking lever 74 engage the outer locking member 76 to move the outer locking member 76 away from the tensioning body 62 such that the locking surface 184 of the outer locking member 76 is moved away from the locking surface 189 of the inner locking member 78. As the band locking lever 74 is rotated towards its locked configuration, the cam bosses 174 engage the outer locking member 76 to move the outer locking member 76 towards the tensioning body 62 such that the locking surface 184 of the outer locking member 76 is moved towards the locking surface 189 of the inner locking member 78. Additionally, the camming surface 176 of the band locking lever 74 may engage the connector 183 of the outer locking member 76 as the band locking lever 74 is rotated towards its locked configuration to move the outer locking member 76 towards the tensioning body 62.

Referring now to FIGS. 5-16, a method of securing a flexible implant system to a bony element with an inserter is disclosed in accordance with the present disclosure. Initially, with reference to FIG. 5, the inserter 10 is positioned over the clamp 12 of a flexible implant system such that the clamp 12 is adjacent the clamp receiver 32 of the distal portion 30 with the securement arm 40 in the intermediate position between the proximal and distal positions such that the clamp lock 50 is pivotable between its secured and unsecured configurations. The inserter 10 is aligned with the clamp 12 such that the upper surface of the clamp 12 is positioned towards the clamp receiver 32 which is sized and shaped to receive the upper surface of the clamp 12. In such an unsecured position of the clamp lock 50, the lock cam pin 54 is moveable within the lock cam channel 48 defined in each of the securement fingers 46 of the securement arms 40.

With particular reference to FIG. 6, the inserter 10 is moved onto the clamp 12 such that the upper surface of the clamp 12 is received within the clamp receiver 32 of the distal portion 30. The securement screw 80 is rotated in a first direction to move the securement arm 40 to its proximal position such that the lock cam pin 54 is engaged by walls of the lock cam channel 48 to move the clamp lock 50 to its unsecured configuration. It is contemplated that the securement fingers 46 may include visual indicia (e.g., a groove 46a in an outer surface of the securement fingers 46) to indicate when the securement arm 40 is in the intermediate position. In the intermediate position, the lock cam pin 54 is engaged with walls defining the lock cam channel 48 such that subsequent proximal movement of the securement arm 40 will move the clamp lock 50 towards its unsecured configuration. In the unsecured configuration of the clamp lock 50, the lock cam pin 54 is positioned within the cam notch 35 of the distal portion 30. As the distal portion 30 engages the clamp 12, the alignment tab 36 of the distal portion 30 engages an alignment notch 14 of the clamp 12 to align the clamp 12 with the distal portion 30.

Figure 7:
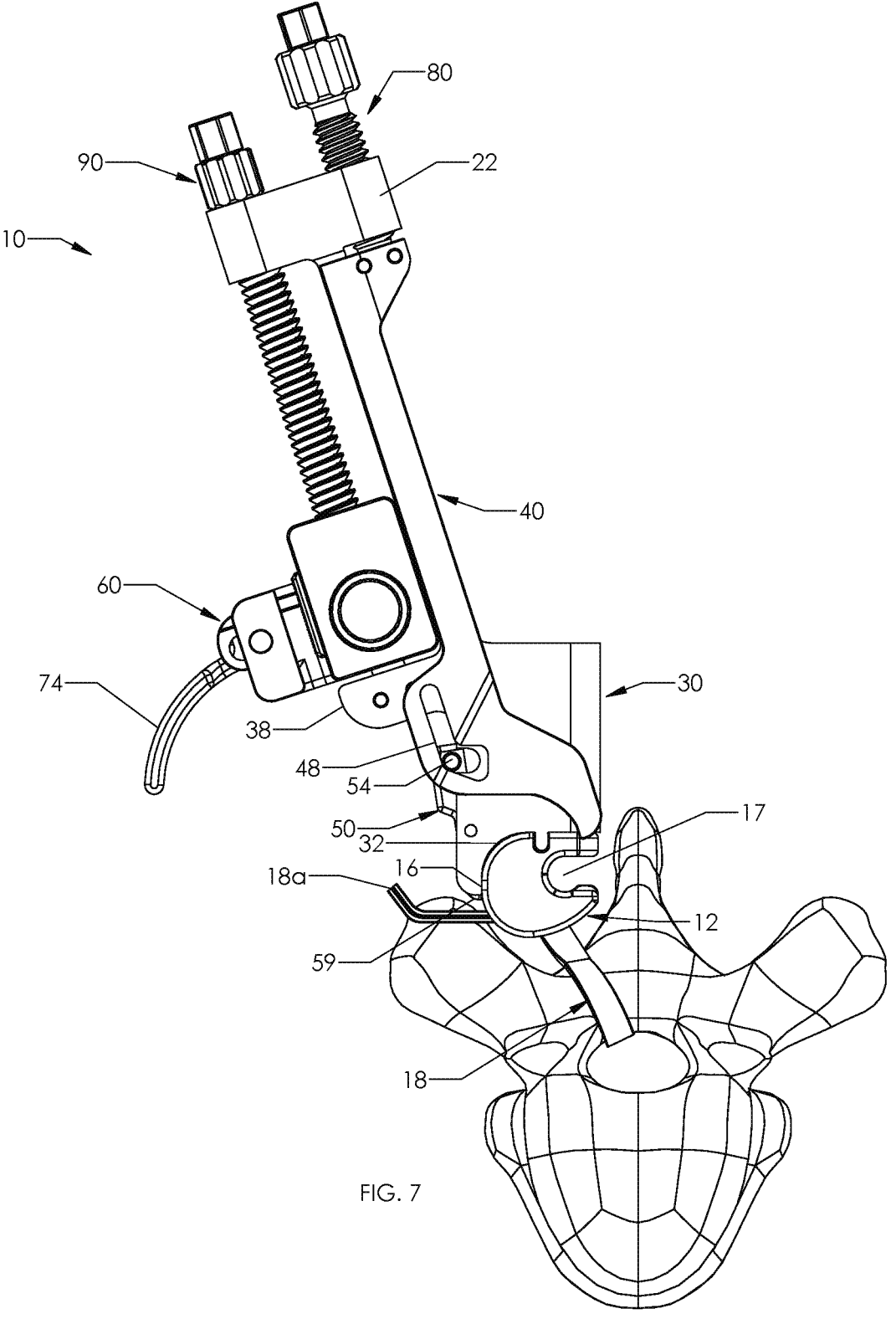
FIG. 7 is a side view of the inserter of FIG. 6 with a flexible band drawn through the clamp, the securement arm of the inserter in the intermediate position, and the clamp lock in a secured configuration.

Referring now to FIG. 7, the securement screw 80 is rotated in a second direction opposite the first direction to move the securement arm 40 towards its secured position until the clamp lock 50 returns to the secured configuration such that the locking tab 59 of the clamp lock 50 engages the securement notch 16 of the clamp 12 to secure the clamp 12 in the clamp receiver 32 of the distal portion 30. The locking tab 59 may provide audible indicia when it engages the securement notch 16.

It is contemplated that the clamp 12 may be secured in the clamp receiver 32 without the securement arm 40 in the unsecured position. For example, with the securement arm 40 in the intermediate position as shown in FIG. 5, as the distal portion 30 engages the clamp 12, the clamp 12 may engage the locking tab 59 of the clamp lock 50 to pivot the clamp lock 50 towards the unsecured configuration against the lock biasing member 51 (FIG. 2) until the securement notch 16 of the clamp 12 is aligned with the locking tab 59. When the securement notch 16 of the clamp 12 is aligned with the locking tab 59, the lock biasing member 51 urges the locking tab 59 into the securement notch 16 to secure the clamp 12 within the clamp receiver 32 of the distal portion 30.

With continued reference to FIG. 7, when the clamp 12 is secured to the inserter 10, ends 18a of a flexible band 18, that is wrapped about a bony element VB, are passed through a slot (not explicitly shown) of the clamp 12. The ends 18a of the flexible band 18 are stacked on top of one another as the flexible band 18 is passed through the slot of the clamp 12.

Referring to FIG. 8, with the flexible band 18 within the slot of the clamp 12, the inserter 10 is used to position a rod 19 (e.g., a spinal rod) within a rod cavity 17 defined by the clamp 12. The clamp 12 may provide audible indicia (e.g., a click) when the rod 19 is received within the rod cavity 17. The ends 18a of the flexible band 18 may be held or pulled as the rod 19 is positioned within the rod cavity 17 to draw slack, excess material, of the flexible band 18 through the slot of the clamp 12.

With reference to FIG. 9, with the rod 19 positioned within the rod cavity 17 of the clamp 12, the securement screw 80 is rotated in the second direction to move the securement arm 40 towards its distal position. As the securement arm 40 moves towards its distal position, the securement fingers 46 engage the rod 19 to secure the rod 19 within the rod cavity 17 of the clamp 12 to prevent the rod 19 from moving out of the rod cavity 17 while allowing clamp 12 to slide over the rod 19 until the clamp is locked to the rod 19 as detailed below. Further, as the securement arm 40 moves towards its distal position, the lock cam channel 48 moves over the lock cam pin 54 such that the walls defining the lock cam channel 48 engage the lock cam pin 54 to prevent the clamp lock 50 from pivoting towards the unsecured configuration (FIG. 6). As such, when the securement arm 40 is in its distal position, the clamp 12 is fully secured in the clamp cavity 32 of the distal portion 30 and the rod 19 is secured in the rod cavity 17 of the clamp 12.

Figure 10:
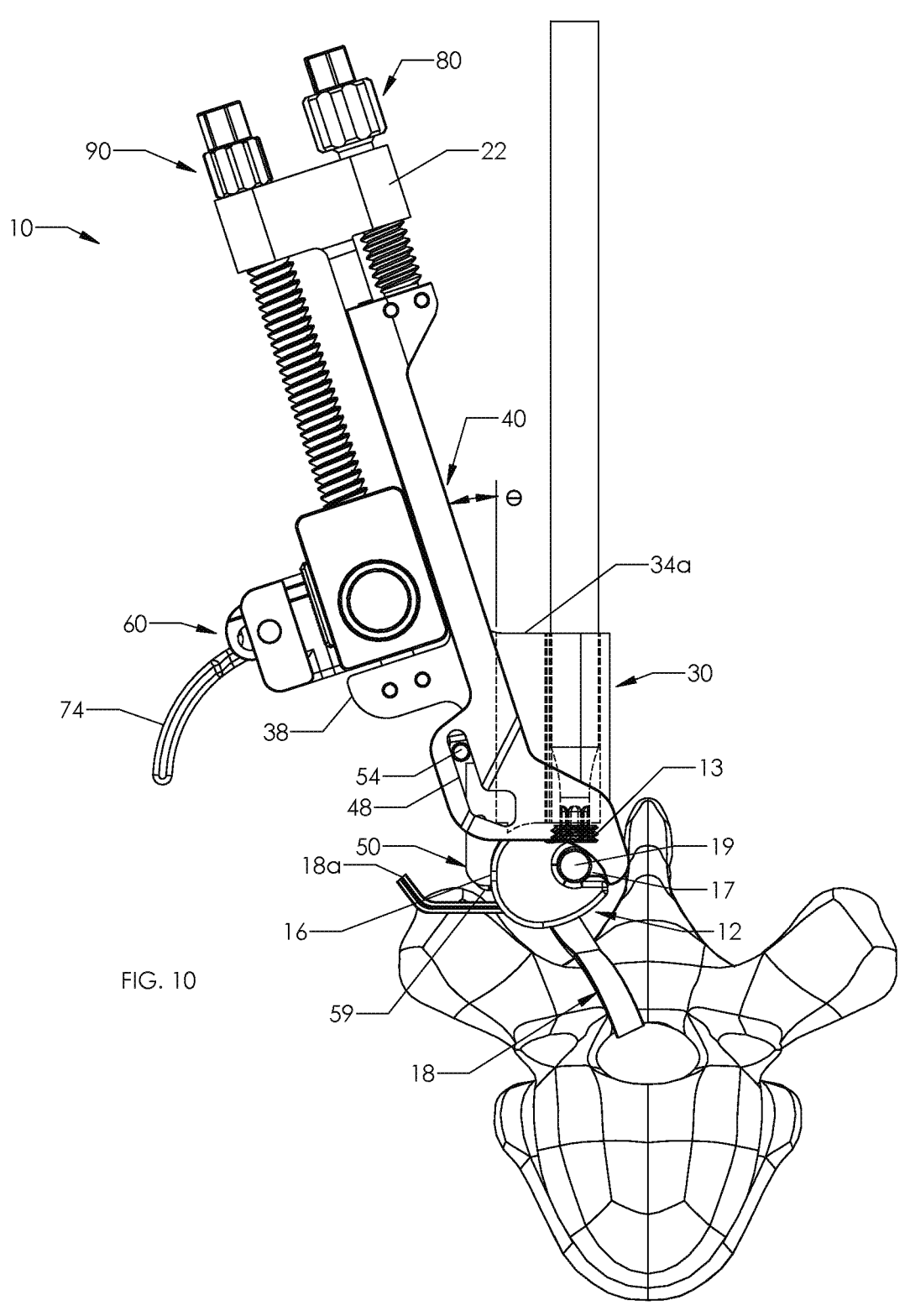
FIG. 10 is a side view of the inserter of FIG. 9 with a tool inserted through the inserter to partially secure the clamp to the rod.

Referring to FIG. 10, with the securement arm 40 in its distal position, a tool 200 may be inserted through the tool opening 34b of the distal portion 30 to engage a rod set screw 13 of the clamp 12. The tool 200 is rotated to rotate the rod set screw 13 into engagement with the rod 19 to partially secure the clamp 12 to the rod 19. The rod set screw 13 is only partially tightened to permit the clamp 12 to move about the rod 19 (e.g., rotate) as the flexible band 18 is fully tensioned about the bony element VB as detailed below. Once the rod 19 is partially secured within the clamp 12, the tool 200 is removed from the tool opening 34b.

Figure 11:
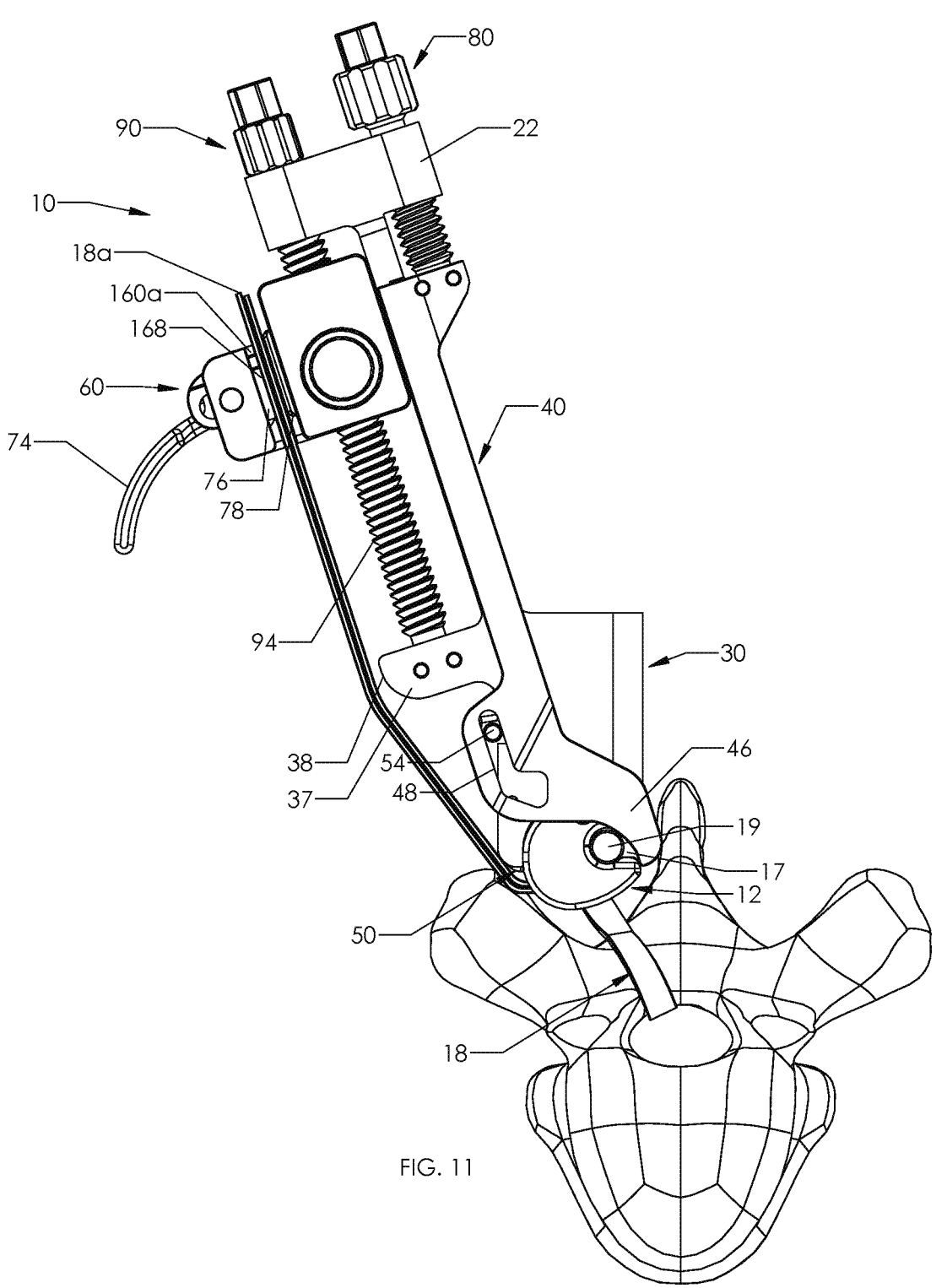
FIG. 11 is a side view of the inserter of FIG. 9 with the flexible band drawn through a band passage of a band locking mechanism which is in an unlocked configuration and a tensioning assembly in a proximal position.

With reference to FIGS. 11 and 12, the flexible band 18 is positioned within the band passage 168 of the tensioning assembly 60. To position the flexible band 18 within the band passage 168 of the tensioning assembly 60, the band locking lever 74 is rotated to the unlocked configuration to move the outer locking member 76 away from the inner locking member 78. With the band locking lever 74 in the unlocked configuration, the flexible band 18 is positioned in the band passage 168 and between the locking surfaces 184, 189 (FIGS. 3 and 4) of the inner and outer locking members 76, 78, respectively. The flexible band 18 may abut the first support arm 160a to backstop the flexible band 18 within the band passage 168. The flexible band 18 may also be positioned in the band recess 38 of the tensioning screw securement arm 37 of the distal portion 30. The flexible band 18 may be positioned within the band passage 168 with the tensioning assembly 60 positioned anywhere along the tensioning screw 90 between its proximal position (FIG. 11) and its distal position (FIG. 12).

With the flexible band 18 positioned within the band passage 168, the tensioning assembly 60 is moved to its distal position as shown in FIG. 12. The tensioning assembly 60 may be moved to its distal position by rotating the tensioning screw 90 until the tensioning assembly 60 abuts the tensioning screw securement arm 37. Alternatively, the tensioning assembly 60 may be moved to its distal position by depressing the button 64 to the depressed position, as detailed above, to disengage the threads of the second wall 153b from the threads of the tensioning screw 90 and sliding the tensioning assembly 60 into abutment with the tensioning screw securement arm 37 before releasing the button 64. When the button 64 is released, the button biasing member 66 urges the button 64 to the disengaged position such that the threads of the second wall 153b engage the threaded body 94 of the tensioning screw 90.

Referring to FIG. 13, with the flexible band 18 positioned in the band passage 168 and the tensioning assembly 60 in its distal position, the band locking lever 74 is rotated to the locked configuration such that the outer locking member 76 is moved towards the inner locking member 78. As the outer locking member 76 is moved towards the inner locking member 78, the locking surfaces 184, 189 (FIGS. 3 and 4) of the inner and outer locking members 76, 78, respectively, engage the flexible band 18 to fix the flexible band 18 relative to the tensioning assembly 60. The ends 18a of the flexible band 18 are pulled by hand until slack or excess material of the flexible band 18 is drawn through the slot of the clamp 12 before the band locking lever 74 is rotated to the locked configuration. Additionally, the ends 18a of the flexible band 18 may be pulled by hand to tension the flexible band 18 about the bony element VB before the band locking lever 74 is rotated to the locked configuration.

Figure 14:
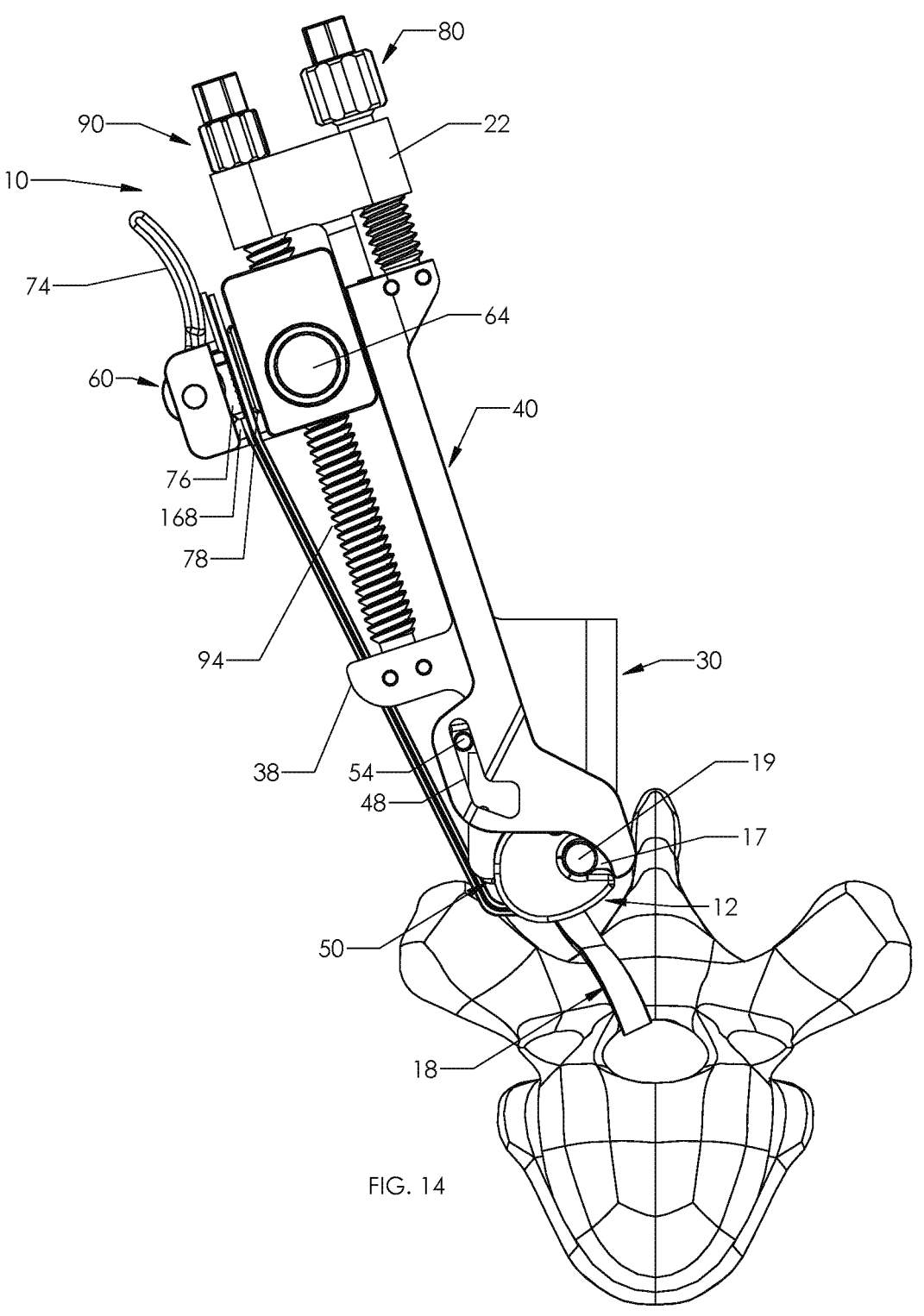
FIG. 14 is a side view of the inserter of FIG. 13 with the tensioning assembly translated to the proximal position with the flexible band fixed to the tensioning assembly.

With reference to FIG. 14, with the flexible band 18 fixed within the band locking mechanism 70 of the tensioning assembly 60, the tensioning screw 90 is rotated to translate the tensioning assembly 60 towards its proximal position. As the tensioning assembly 60 is translated towards its proximal position, the flexible band 18 is drawn through the slot of the clamp 12 and is tensioned about a bony element VB. The tensioning assembly 60 is translated until the flexible band 18 is reduced and fully tensioned about the bony element VB.

Figure 15:
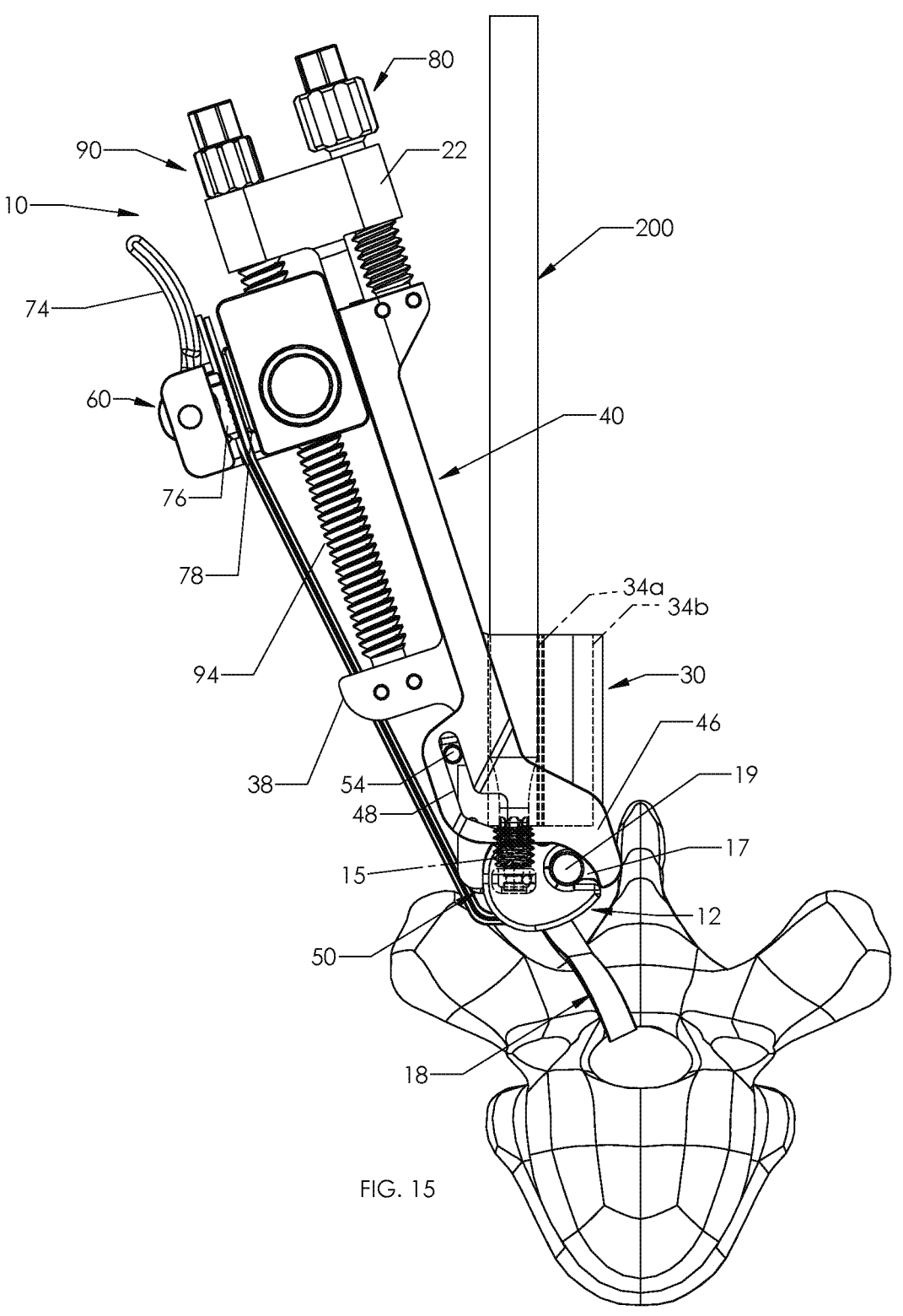
FIG. 15 is a side view of the inserter of FIG. 14 with a tool inserted through the inserter to fix the flexible band to the clamp.

Referring to FIG. 15, it is contemplated that the flexible band 18 may need to be tensioned more than tension applied to the flexible band 18 by a single translation of the tensioning assembly 60 from its distal position to its proximal position such that multiple translations of the tensioning assembly 60 are required. In such instances, the tool 200 is inserted through the tool passage 34*a* of the distal portion 30 to engage a band set screw 15 of the clamp 12 when the tensioning assembly 60 is in its proximal position. The tool 200 is then rotated to rotate the band set screw 15 to at least partially fix the flexible band 18 within the slot of the clamp 12. With the flexible band 18 at least partially fixed, the band locking lever 74 is rotated to the unlocked configuration and the tensioning assembly 60 is translated to its proximal position. As detailed above, the tensioning assembly 60 may be translated by rotating the tensioning screw 90 or by depressing the button 64. With the tensioning assembly 60 in its distal position, the band locking lever 74 is rotated to the locked configuration to fix the flexible band 18 to the tensioning assembly 60. With the flexible band 18 fixed to the tensioning assembly 60, the tool 200 is rotated to rotate the band set screw 15 such that the flexible band 18 is free to slide within the slot of the clamp 12. The tensioning screw 90 is then rotated again to translate the tensioning assembly 60 towards its proximal position to draw the flexible band 18 through the slot of the clamp to reduce and tension the flexible band 18 about the bony element VB. This process is repeated until the flexible band 18 is fully reduced and tensioned about the bony element VB with a desired amount of tension.

When the flexible band 18 is fully tensioned, the tool 200 is inserted through the tool opening 34*b* of the distal portion to engage the rod set screw 13 of the clamp 12 as shown in FIG. 11. The tool 200 is rotated to fully tighten the rod set screw 13 to the rod 19 to fix the clamp 12 to the rod 19. The tool 200 is then removed from the tool opening 34*b* and inserted through the tool opening 34*a* to engage the band set screw 15. The tool 200 is then rotated to fully tighten the band set screw 15 to fix the flexible band 18 within the slot of the clamp 12.

Figure 16:
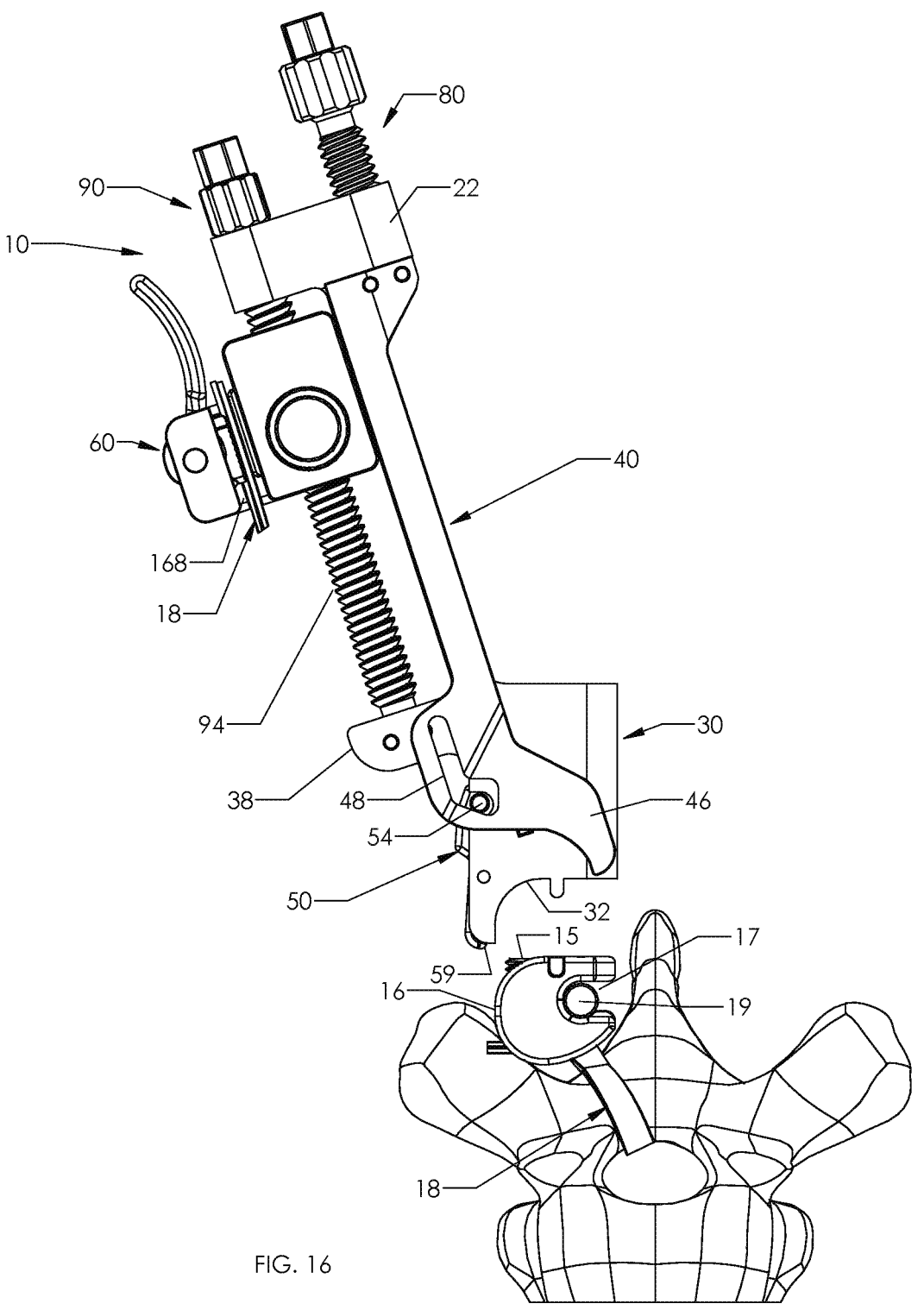
FIG. 16 is a side view of the inserter of FIG. 15 released from the clamp and the flexible band trimmed to length.

Referring to FIG. 16, with the clamp 12 fixed to the rod 19 and the flexible band 18 fixed within the slot of the clamp 12, the flexible band 18 is cut to length adjacent the clamp 12. It is contemplated that the flexible band 18 is cut in a range of about 0.1 cm to about 2.0 cm from the clamp 12 (e.g., 1.0 cm). It is further contemplated that the band locking lever 74 may be rotated to the unlocked configuration and/or the tensioning assembly 60 may be moved towards its distal position, by rotation of the tensioning screw 90 and/or depressing the button 64 as detailed above, to remove tension from the flexible band 18 after the band set screw 15 fixes the flexible band 18 within the slot and before the flexible band 18 is cut to length.

When the flexible band 18 is cut to length, the securement screw 80 is rotated to translate the securement arm 40 to its proximal position such that the securement fingers 46 are withdrawn from over the rod recess 17 of the clamp 12. As detailed above, as the securement arm 40 reaches its proximal position, the walls defining the lock cam channel 48 engage lock cam pin 54 to pivot the clamp lock 50 to the unsecured configuration. With the securement arm 40 in its proximal position, the clamp 12 is released from the clamp receiver 32 of the distal portion 30 of the inserter 10.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument, comprising:
a body defining a longitudinal axis;
a tensioning assembly configured to engage a flexible implant;
a first actuator rotatable about a rotation axis offset from the longitudinal axis, the rotatable actuator configured to move the tensioning assembly to tension the flexible implant;
a second actuator that, when pressed toward the surgical instrument, is configured to release tension on the flexible implant,
wherein the rotation axis extends parallel to the longitudinal axis.

2. The surgical instrument of claim 1, wherein the tensioning assembly includes a pair of opposing clamping members configured to releasably hold the flexible implant.

3. The surgical instrument of claim 2, wherein the pair of opposing clamping members include textured surfaces positioned within a band passage configured to improve a grasp of the flexible implant.

4. The surgical instrument of claim 3, wherein the pair of opposing clamping members are configured to transition between a secured configuration and an unsecured configuration for securing the flexible implant and releasing the flexible implant, respectively.

5. The surgical instrument of claim 1, wherein the first actuator is proximal to the tensioning assembly.

6. The surgical instrument of claim 1, wherein the first actuator is coupled to an extension projecting from the body.

7. The surgical instrument of claim 6, wherein the extension is a securement element coupled to a distal end of the rotatable actuator and configured to support the rotatable actuator.

8. The surgical instrument of claim 1, wherein the tensioning assembly is translatable along a direction parallel to the rotation axis.

9. A method of performing surgery, comprising:
positioning a distal portion of a surgical instrument in engagement with a first implant, the surgical instrument defining a longitudinal axis;
engaging at least a portion of a flexible implant with a tensioning assembly of the surgical instrument; and
rotating a first actuator about a rotation axis offset from the longitudinal axis to move the tensioning assembly to tension the flexible implant;
a second actuator that, when pressed toward the surgical instrument, is configured to release tension on the flexible implant,
wherein the rotation axis extends parallel to the longitudinal axis.

10. The method of claim 9, further comprising implanting the first implant within a patient before the step of positioning the surgical instrument in engagement with the first implant.

11. The method of claim 9, further comprising securing the portion of the flexible implant with an opposing pair of clamping members of the surgical instrument.

12. The method of claim 9, further comprising securing the portion of the flexible implant within a band lock of the surgical instrument.

13. The method of claim 12, wherein securing the portion of the flexible implant within the band lock includes passing ends of the flexible implant through a band passage defined by the band lock.

14. The method of claim 12, wherein securing the portion of the flexible implant within the band lock of the surgical instrument includes clamping the flexible implant between textured surfaces of opposing clamp members included on the band lock.

15. The method of claim 12, wherein securing the portion of the flexible implant within the band lock includes transitioning the band lock to a locked configuration to fix the flexible band relative to the band lock.

16. The method of claim 9, further comprising passing ends of the flexible implant through the first implant.

17. The method of claim 9, further comprising securing the first implant to the flexible implant.

18. The method of claim 17, further comprising trimming the flexible implant to a length adjacent the first implant after securing the flexible implant to the first implant.

* * * * *